US010632113B2

United States Patent
Vaka et al.

(10) Patent No.: US 10,632,113 B2
(45) Date of Patent: Apr. 28, 2020

(54) ABUSE-RESISTANT DRUG FORMULATIONS WITH BUILT-IN OVERDOSE PROTECTION

(71) Applicant: KASHIV BIOSCIENCES, LLC, Bridgewater, NJ (US)

(72) Inventors: Siva Ram Kiran Vaka, Piscataway, NJ (US); Ashish Chatterji, East Brunswick, NJ (US); Dipen Desai, Bridgewater, NJ (US); Wantanee Phuapradit, Montville, NJ (US); Navnit H. Shah, Clifton, NJ (US); Atsawin Thongsukmak, Piscataway, NJ (US); Kanji Meghpara, Morris Plains, NJ (US)

(73) Assignee: KASHIV BIOSCIENCES, LLC, Bridgewater, NJ (US)

( * ) Notice: Subject to any disclaimer, the term of this patent is extended or adjusted under 35 U.S.C. 154(b) by 0 days.

(21) Appl. No.: 15/117,114

(22) PCT Filed: Feb. 5, 2015

(86) PCT No.: PCT/US2015/014690
§ 371 (c)(1),
(2) Date: Aug. 5, 2016

(87) PCT Pub. No.: WO2015/120201
PCT Pub. Date: Aug. 13, 2015

(65) Prior Publication Data
US 2016/0346274 A1  Dec. 1, 2016

Related U.S. Application Data

(60) Provisional application No. 61/935,971, filed on Feb. 5, 2014.

(51) Int. Cl.
*A61K 31/485* (2006.01)
*A61K 9/20* (2006.01)
(Continued)

(52) U.S. Cl.
CPC .......... *A61K 31/485* (2013.01); *A61K 9/0053* (2013.01); *A61K 9/2077* (2013.01);
(Continued)

(58) Field of Classification Search
None
See application file for complete search history.

(56) References Cited

U.S. PATENT DOCUMENTS 4,800,083 A   1/1989  Hom et al.
6,488,963 B1  12/2002 McGinity et al.
(Continued)

FOREIGN PATENT DOCUMENTS

WO   WO 2011/066980 A2   6/2011
WO   WO 2013/128276 A2   9/2013
(Continued)

OTHER PUBLICATIONS

International Search Report and Written Opinion dated Apr. 29, 2015 in International Application No. PCT/US15/14690.

*Primary Examiner* — Isis A Ghali
(74) *Attorney, Agent, or Firm* — Baker Botts L.L.P.

(57) ABSTRACT

Disclosed are solid oral pharmaceutical compositions that that are intended to provide protection against overdose and tampering, as well as abuse deterrence. The compositions contain a plurality of granules or multi-particulates. A first population of multi particulates contains an API or drug susceptible to abuse, a polymer matrix, and an outer coating that contains a cationic pH dependent polymer. These multi particulates also contain a plasticizer and a surfactant. A second population of multi particulates contains a viscosity building polymer and an alkaline buffering agent. Compositions may further include a disintegrant, and/or additional viscosity building polymers and/or alkaline buffering agents
(Continued)

DISPERSION OF MULTI-PARTICULATES A IN THE GI TRACT
(ONE UNIT DOSE VS MULTIPLE UNIT DOSES)

MULTIPLE UNITS TAKEN and/or ion exchange polymers. Also disclosed are the methods of making and using the compositions.

24 Claims, 8 Drawing Sheets

(51) Int. Cl.
*A61K 9/50* (2006.01)
*A61K 31/4439* (2006.01)
*A61K 9/00* (2006.01)
*A61K 9/48* (2006.01)
*A61K 9/51* (2006.01)

(52) U.S. Cl.
CPC .............. *A61K 9/2081* (2013.01); *A61K 9/48* (2013.01); *A61K 9/501* (2013.01); *A61K 9/5015* (2013.01); *A61K 9/5026* (2013.01); *A61K 9/5073* (2013.01); *A61K 9/5078* (2013.01); *A61K 9/5084* (2013.01); *A61K 9/5115* (2013.01); *A61K 9/5123* (2013.01); *A61K 9/5138* (2013.01); *A61K 9/5161* (2013.01); *A61K 31/4439* (2013.01); *A61K 9/5047* (2013.01)

(56) References Cited

U.S. PATENT DOCUMENTS

| | | | |
|---|---|---|---|
| 7,201,920 B2 | 4/2007 | Kumar et al. | |
| 7,476,402 B2 | 1/2009 | Kumar et al. | |
| 7,510,726 B2 | 3/2009 | Kumar et al. | |
| 7,674,799 B2 | 3/2010 | Chapman et al. | |
| 7,674,800 B2 | 3/2010 | Chapman et al. | |
| 7,683,072 B2 | 3/2010 | Chapman et al. | |
| 7,776,314 B2 | 8/2010 | Bartholomäus | |
| 7,981,439 B2 | 7/2011 | Kumar et al. | |
| 8,075,872 B2 | 12/2011 | Arkenau-maric et al. | |
| 8,101,630 B2 | 1/2012 | Kumar et al. | |
| 8,114,383 B2 | 2/2012 | Bartholomäus et al. | |
| 8,187,636 B2 | 5/2012 | Soscia et al. | |
| 8,309,060 B2 | 11/2012 | Bartholomaus et al. | |
| 8,337,888 B2 | 12/2012 | Wright et al. | |
| 8,349,362 B2 | 1/2013 | Soscia et al. | |
| 8,409,616 B2 | 4/2013 | Kumar et al. | |
| 8,507,001 B2 | 8/2013 | Shukla et al. | |
| 8,637,540 B2 | 1/2014 | Kumar et al. | |
| 8,808,741 B2 | 8/2014 | McKenna et al. | |
| 8,871,265 B2 | 10/2014 | Wright et al. | |
| 8,894,987 B2 | 11/2014 | McKenna et al. | |
| 8,894,988 B2 | 11/2014 | McKenna et al. | |
| 9,034,376 B2 | 5/2015 | Wright et al. | |
| 9,060,976 B2 | 6/2015 | Wright et al. | |
| 9,073,933 B2 | 7/2015 | Chapman et al. | |
| 9,101,636 B2 | 8/2015 | Brzeczko et al. | |
| 9,216,176 B2 | 12/2015 | Habib et al. | |
| 9,248,195 B2 | 2/2016 | Rariy et al. | |
| 9,320,796 B2 | 4/2016 | Brzeczko et al. | |
| 9,375,428 B2 | 6/2016 | Fischer et al. | |
| 9,387,166 B2 | 7/2016 | Rey et al. | |
| 9,492,389 B2 | 11/2016 | McKenna et al. | |
| 9,492,391 B2 | 11/2016 | McKenna et al. | |
| 9,492,392 B2 | 11/2016 | McKenna et al. | |
| 9,492,393 B2 | 11/2016 | McKenna et al. | |
| 9,492,443 B2 | 11/2016 | Kumar et al. | |
| 2003/0175336 A1 | 9/2003 | Luber et al. | |
| 2004/0131552 A1* | 7/2004 | Boehm | A61K 9/2077 424/10.1 |
| 2006/0105038 A1 | 5/2006 | Lai et al. | |
| 2006/0110327 A1* | 5/2006 | Emigh | A61K 9/0043 424/10.2 |
| 2006/0204585 A1* | 9/2006 | Hall | A61K 9/0056 424/489 |
| 2008/0020018 A1 | 1/2008 | Moodley et al. | |
| 2008/0069878 A1 | 3/2008 | Venkatesh et al. | |
| 2008/0069891 A1* | 3/2008 | Habib | A61K 9/1652 424/494 |
| 2008/0075768 A1 | 3/2008 | Vaughn et al. | |
| 2009/0232887 A1 | 9/2009 | Odidi et al. | |
| 2009/0258066 A1* | 10/2009 | Venkatesh | A61K 9/0056 424/462 |
| 2010/0099696 A1 | 4/2010 | Soscia et al. | |
| 2010/0260844 A1 | 10/2010 | Scicinski et al. | |
| 2010/0291183 A1 | 11/2010 | Farrell et al. | |
| 2011/0129530 A1 | 6/2011 | Venkatesh et al. | |
| 2011/0142942 A1 | 6/2011 | Schobel et al. | |
| 2012/0202839 A1 | 8/2012 | Emigh et al. | |
| 2013/0136797 A1 | 5/2013 | Mehta et al. | |
| 2013/0330409 A1* | 12/2013 | Mohammad | A61K 9/1635 424/489 |
| 2014/0155388 A1 | 6/2014 | Brzeczko et al. | |
| 2014/0322311 A1 | 10/2014 | Ashworth et al. | |
| 2015/0017240 A1 | 1/2015 | Shah et al. | |
| 2015/0030677 A1 | 1/2015 | Adjei et al. | |
| 2015/0118295 A1 | 4/2015 | Haswani et al. | |
| 2015/0118300 A1 | 4/2015 | Haswani et al. | |
| 2015/0118301 A1 | 4/2015 | Haswani et al. | |
| 2015/0265596 A1 | 9/2015 | Hirsh et al. | |
| 2015/0272902 A1 | 10/2015 | Dharmadhikari et al. | |
| 2015/0283086 A1 | 10/2015 | Arkenau-maric et al. | |
| 2015/0313845 A1 | 11/2015 | Bartholomäus et al. | |
| 2015/0320689 A1 | 11/2015 | Dharmadhikari et al. | |
| 2015/0335592 A1 | 11/2015 | Barnscheid et al. | |
| 2015/0374630 A1 | 12/2015 | Arkenau-maric et al. | |
| 2016/0022587 A1 | 1/2016 | Arkenau-maric et al. | |
| 2016/0022590 A1 | 1/2016 | Odidi | |
| 2016/0101022 A1 | 4/2016 | Arkenau-maric et al. | |
| 2016/0106839 A1 | 4/2016 | Barnscheid et al. | |
| 2016/0175256 A1 | 6/2016 | Bartholomäus et al. | |
| 2016/0184295 A1 | 6/2016 | Bartholomäus et al. | |
| 2016/0199388 A1 | 7/2016 | Brzeczko et al. | |
| 2016/0250203 A1 | 9/2016 | Haswani et al. | |
| 2016/0256392 A1 | 9/2016 | Haswani et al. | |
| 2016/0271066 A1 | 9/2016 | Barnscheid et al. | |
| 2016/0317457 A1 | 11/2016 | Haswani et al. | |

FOREIGN PATENT DOCUMENTS

| | | | |
|---|---|---|---|
| WO | WO 2014/145195 A1 | 9/2014 | |
| WO | WO 2016/094358 A1 | 6/2016 | |

* cited by examiner

IMMEDIATE-RELEASE OF API FROM MULTI-PARTICULATES A WHEN EXPOSED TO GASTRIC FLUID

EXTENDED-RELEASE OF API FROM MULTI-PARTICULATES A WHEN EXPOSED TO INTESTINAL FLUID

ER DRUG RELEASE FROM THE PARTICULATE WHEN EXPOSED TO INTESTINAL FLUID

DISPERSION OF MULTI-PARTICULATES A IN THE GI TRACT
(ONE UNIT DOSE VS MULTIPLE UNIT DOSES)

A UNIT DOSE TAKEN

DISPERSION OF MULTI-PARTICULATES A IN THE GI TRACT
(ONE UNIT DOSE VS MULTIPLE UNIT DOSES)

MULTIPLE UNITS TAKEN

RHEOLOGY PROFILE OF VISCOSITY BUILDING POLYMER
(VISCOSITY ON Y-AXIS, NUMBER OF DOSES ON X-AXIS)

$C_{max}$ VS OPIOID DOSE (NON-ABUSE-RESISTANT FORMULATION VS. INVENTIVE FORMULATION)

INCREASE IN pH OF GASTRIC FLUID WITH MULTIPLE DOSES
(pH ON Y-AXIS, NUMBER OF DOSES ON X-AXIS)

SCHEMATIC REPRESENTATION OF ONE OF THE EMBODIMENTS
OF MULTI-PARTICULATE A.

THE EFFECT OF SINGLE DOSE VS MULTIPLE DOSES ON
THE % DRUG BONDED TO AMBERLITE AT DIFFERENT pH CONDITIONS.

ABUSE-RESISTANT DRUG FORMULATIONS WITH BUILT-IN OVERDOSE PROTECTION

CROSS-REFERENCE TO RELATED APPLICATION

The present application is a U.S. National Stage Patent Application under 35 U.S.C. § 371 of International Application No. PCT/US2015/014690, filed on Feb. 5, 2015, which claims the benefit of the filing date of U.S. Provisional Application No. 61/935,971, filed Feb. 5, 2014, entitled ABUSE-RESISTANT DRUG FORMULATIONS WITH BUILT-IN OVERDOSE PROTECTION, the disclosure of each of which is hereby incorporated herein by reference.

BACKGROUND OF THE INVENTION

Governmental reports state that prescription drug abuse is the fastest growing drug problem in the United States, and a survey indicated that nearly one-third of people age 12 and above who used drugs illicitly for the first time in 2009 began by the non-medical use of a prescription drug. The problem has been exacerbated by the introduction of controlled-release opioid products that contain higher amounts of their active ingredients, beginning with an oxycodone product that was approved for marketing in 1995. Reports of overdosing and death from prescription pain products, especially the controlled-release oxycodone product, rose sharply in the early 2000s.

Overdose incidence of the opioid dosage forms is summarized in Table 1 below.

TABLE 1

Overdose incidence of opioid dosage forms

| Product | Overdose (%) |
|---|---|
| Hydrocodone/APAP-Immediate Release | 23 |
| Oxycodone/APAP-Immediate Release | 11 |
| Oxycodone Immediate Release | 7 |
| Oxycodone Extended Release | 4 |

In January 2013, the U.S. Food and Drug Administration published a draft guidance document for the evaluation and labeling of abuse-resistant opioid products. The guidance states that opioid analgesics can be abused by: swallowing whole in excessive quantities; crushing and swallowing; crushing and inhaling nasally ("snorting"); crushing and smoking; or crushing, dissolving, and injecting. Categories of abuse-resistant formulations were described as:
1. Physical barriers to prevent chewing, crushing, cutting, grating or grinding, and chemical barriers to resist extraction of the active ingredient with common solvents such as water, alcohol, and organic liquids;
2. Agonist/antagonist combinations that interfere with, reduce, or defeat the euphoria associated with abuse;
3. Aversion, by incorporating a substance that produces an unpleasant effect when the dosage form is altered before ingestion, or is ingested in a high dose;
4. Delivery systems that provide abuse resistance through release characteristic design or a mode of administration;
5. Pro-drugs that lack opioid activity until acted upon in the gastrointestinal system; and
6. Combinations of two or more of the foregoing.

The FDA describes the science of abuse deterrence as relatively new and rapidly evolving. A few abuse-resistant opioid products are currently approved for marketing. Some of these products are OxyContin® (oxycodone hydrochloride extended-release tablets), Targiniq® (oxycodone HCL+ naloxone HCL), and Embeda® (morphine sulfate and naltrexone hydrochloride). Other products such as Suboxone® and Opana ER® (oxymorphone) also purport to have abuse deterrent properties but do not have a formal claim on the label. The oxycodone hydrochloride extended-release tablets, sold by Purdue Pharma L.P. under the tradename OxyContin® in strengths of 10, 15, 20, 30, 40, 60, and 80 mg, are formulated to have a high hardness to resist crushing, breaking, and dissolution, and also forms a viscous hydrogel in aqueous media that inhibits passage of an extract through a needle.

In general, abusers of opioid drugs do not ingest more than a typical therapeutic dose because the controlled-release formulations do not provide bursts of drug bioavailability to create the desired euphoric sensations. Rather, abuse tends to involve some physical manipulation of a dosage form so that larger amounts of immediately available drug can be taken orally, nasally, or by intravenous injection. For this reason, the OxyContin tablets are formed from a partially molten mixture that contains a high molecular weight polyethylene oxide excipient; the result is a tablet that is not easily powdered and cannot readily be modified to form a solution that is capable of being injected. The very high hardness of this product, however, would not permit reproducible splitting of a dosage form to administer a reduced dose or improve the administration for those having difficulty in swallowing.

A need remains for improved formulations that make it difficult, if not impossible, for individuals to misuse particularly from the standpoints of extracting the drug from multiple doses and ingesting multiple doses. In particular, new formulations are needed which can be used with immediate release and extended release pharmaceutical products. Such formulations, while having abuse-resistant properties, must also allow for the active pharmaceutical ingredient to be soluble in the gastrointestinal tract and have the desired pharmacological activity. In the case of opioids, the pharmacological activity would be an analgesic effect.

BRIEF SUMMARY OF THE INVENTION

Aspects of the present invention provide compositions that contain drugs susceptible to abuse and which are formulated to resist attempts to administer the active ingredients by non-indicated routes and/or in large doses. The inventive compositions may contain ingredients that provide overdose protection, tamper resistance and abuse deterrence when administered in an unprescribed or improper manner. Yet the compositions still release the active pharmaceutical ingredient in the gastrointestinal tract upon ingestion at the recommended dose to allow for the desired pharmacological and therapeutic effect.

A first aspect of the present invention is directed to a solid oral pharmaceutical composition that contains a) a first population of multi-particulates containing a therapeutically effective amount of a drug that is susceptible to abuse, a polymer matrix, and an outer (or functional) coating layer containing a first cationic pH-dependent polymer; wherein the multi-particulates further contain a plasticizer and a surfactant (which also may be aversion agents); and b) a second population of multi-particulates containing a first viscosity-building polymer and a first alkaline buffering agent.

In some embodiments, the composition contains an intermediate coating layer, which may be referred to herein as a sealing layer. Thus, the oral pharmaceutical composition may include the polymer matrix in or as an inner core, and wherein the intermediate coating layer is disposed between the inner core and the outer coating layer, and wherein the intermediate layer contains a first non-ionic pH-independent polymer. The entire amount, i.e., the therapeutically effective amount, of the drug may be contained in the inner core or in the intermediate layer or in some other embodiments, the drug may be contained in both the inner core and the intermediate layer, provided that the total amount of the drug in the composition is therapeutically effective for its intended purpose.

In additional embodiments, the compositions may contain at least one additional ingredient that contributes to the overall overdose protective and/or tamper resistant and/or abuse deterrent properties. Compositions may further include a disintegrant, and/or additional viscosity building polymers and/or alkaline buffering agents and/or ion exchange polymers.

Another aspect of the present invention is directed to a method of formulating a drug that is susceptible to abuse in order to provide abuse deterrence and protection against overdose and tampering, wherein the formulating comprises: a) preparing a first population of multi-particulates comprising a therapeutically effective amount of a drug that is susceptible to abuse, a polymer matrix, and an outer coating layer comprising a first cationic pH-dependent polymer; wherein the multi-particulates further comprise a plasticizer and a surfactant; b) preparing a second population of multi-particulates comprising a first viscosity-building polymer and a first alkaline buffering agent; and c) combining the first and second populations of multi-particulates. The compositions may be formulated by compression into the form of a tablet or by loading into soft or hard gelatin capsules.

A further aspect of the present invention is directed to a method of providing abuse deterrence and protection against overdose and tampering of a drug that is susceptible to abuse, comprising administering the solid oral pharmaceutical composition to a patient in need thereof.

DETAILED DESCRIPTION

The present invention provides solid oral API compositions that prevent or mitigate abuse and/or overdose of an active pharmaceutical ingredient through ingestion of non-prescribed large quantities or by non-prescribed administration routes. The compositions are formulated such that they intend to provide protection from overdose. The compositions may also be formulated such that they resist attempts to extract or otherwise attempt to isolate the active ingredient as a single entity, where that entity could later be abused. As detailed herein, the compositions contain a plurality of populations of multi-particulates.

"Abuse-resistance" and "tamper-resistance" are used interchangeably herein to refer to compositions that reduce the potential for abuse (such as by tampering with the dosage form and/or administering the drug by any route other than prescribed) of drugs but deliver a therapeutically effective dose when administered as directed.

"Overdose" is used herein to refer to taking the compositions in amounts that are non-prescribed.

"Drug", "active agent", "active pharmaceutical ingredient" and "pharmaceutically active ingredient" are used interchangeably herein to refer to a chemical compound that induces a desired pharmacological and/or physiological effect. The terms also encompass pharmaceutically acceptable derivatives of those active agents specifically mentioned herein, including salts, solvates, hydrates, complexes with one or more molecules, pro-drugs, active metabolites, lipophilic derivatives, analogs, and the like.

"Gastric fluid" is used herein to refer to the colorless, watery, acidic digestive fluid that is secreted by various glands in the mucous membrane of the stomach and consists chiefly of hydrochloric acid, pepsin, rennin, and mucin.

A "multi-particulate" is used herein to refer to a discrete, small, repetitive unit of particles or granules that include at least one excipient, and optionally an active pharmaceutical ingredient. Thus, the populations of multi-particulates that do not contain a drug may also be referred to herein as populations of micro-particles. "Multi-particulate drug delivery systems" refer to oral dosage forms that include a multiplicity of populations of small discrete units or granules.

Figure 1:
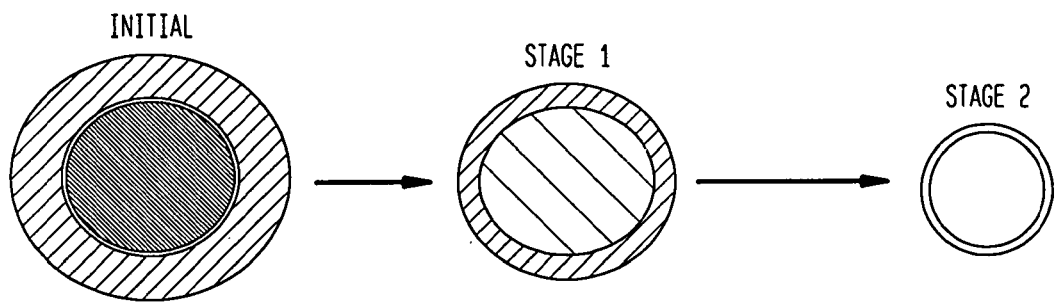
FIG. 1 is a schematic diagram showing immediate-release of API from multi-particulate A when exposed to gastric fluid, wherein in stage 1 the membrane-coat of Eudragit E begins dissolving and the API starts diffusing out rapidly therefrom, and in stage 2 the membrane-coat of Eudragit E has completely dissolved and the API has rapidly released from polymer matrix by diffusion and/or erosion.

The term "immediate release" as used herein means that the bulk of the drug is released from the dosage form in which it is administered in the stomach (e.g., as illustrated in FIG. 1). By "bulk," it is meant that at least about 50% of the drug should be released within 60 minutes. In many cases, that release will be as quickly as practicable, i.e., dissolution will be as close to that resulting from administering an equal amount of fine loose powder."

Figure 2:
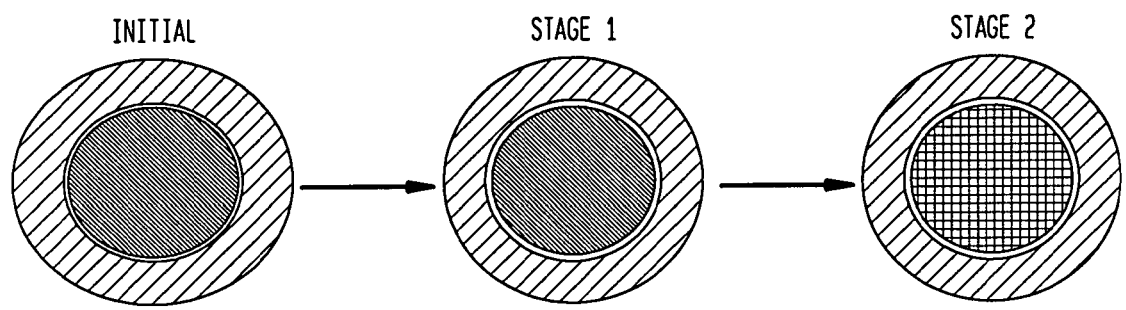
FIG. 2 is a schematic diagram showing extended-release of API from multi-particulate A when exposed to intestinal fluid, wherein in stage 1, the membrane-coat of Eudragit E starts hydrating but is not soluble, and the drug is slowly diffusing therefrom, and in stage 2 the membrane-coat of Eudragit E remains intact and acts as a membrane barrier for the API to slowly permeate therefrom.

The term "extended release" as used herein means that the composition is formulated to make the drug available over a greater period of time after ingestion thereby allowing a reduction in dosing frequency, as compared to a drug presented as a conventional dosage form (e.g., as a solution or an immediate release dosage form) (e.g., as illustrated in FIG. 2).

The term "solid" as used herein means that the composition has no measurable viscosity at room temperature.

Formulations of the present invention are obtained using combinations of agents that individually and collectively impart advantageous properties namely overdose protection, abuse/tamper-resistance, and in some other embodiments, abuse deterrence/aversion.

The effects that are obtainable with the present invention described herein may include:

1. Oral Route: When overdose manipulation occurs, the pharmaceutical compositions disclosed herein provide: (i) an increase in viscosity of a solution due to the presence of the viscosity-building polymer, and (ii) a transient increase in pH in the gastric fluid due to the alkaline buffering agent (as well as any acid suppressing agent that may be present), which in turn will suppress the dissolution rate of the drug through the cationic pH-dependent polymer present in the functional membrane coat in the multi-particulates. Based on the above mechanisms, it is believed that the formulation will reduce, block, or mitigate the effect of the opioid via overdose orally.

2. Nasal Route: Due to their severe nasal irritation and/or with unpleasant effect, one or more aversion agents that may be present in the formulation will result in noxious effects upon insufflation when the product is manipulated for administration by the nasal route. For example in some embodiments, due to both high boiling points and good solubilization properties of some surfactants, the formulation will deter abusers from vaporizing for inhalation, as the vaporization temperatures are relatively high and can induce drug degradation, thus inhibiting pharmacological effects to an abuser. The extent of the crush-resistance of the composition does not allow for reducing the size of the multi-particulates A to a size that can be taken nasally.

3. Injection Route: Due to their surface active properties, surfactants can cause deterrent effects, such as tissue irritation and/or pain at sites of injection. Due to the viscosity building properties, polymers can cause abuse resistance effects such as gelling.

The formulations of the present disclosure are designed to suppress or mitigate the release of the active pharmaceutical ingredient when excessive quantities are ingested. The formulations in the present disclosure are designed not to contribute any adverse effects when administered at recommended doses using the recommended route of administration; however they will produce noxious effects upon manipulation via nasal and injection routes of administration. In one embodiment, the solid pharmaceutical compositions contain two populations of multi-particulates, namely a first population of multi-particulates A and a second population of multi-particulates B.

Composition of Multi-Particulate A

Multi-particulates A are at least partially crush-resistant, and in some embodiments are substantially crush resistant. They cannot be further pulverized into fine powder by mechanical grinding, preventing the abuser from manipulation by snorting via nasal route of administration. The multi-particulates include an active pharmaceutical ingredient, a polymer matrix that in some embodiments may include a cationic pH-dependent or a nonionic pH-independent polymer, a plasticizer, a surfactant, and an outer coating layer that includes a cationic pH-dependent polymer, which may be the same or different as the cationic pH-dependent polymer contained in the polymer matrix. In some embodiments, the therapeutically effective amount of the drug and the polymer matrix are contained in an inner core. The plasticizer may be contained in the inner core, the outer coating layer, or both the inner core and the outer coating layer (in the same or different amounts). The cationic pH-dependent polymer allows rapid drug release in the gastric fluid but retards drug release in the intestinal fluids. Likewise, the surfactant may be contained in the inner core, the outer coating layer, or in both the inner core and the outer coating layer (in the same or different amounts).

Suitable APIs for preparing formulations of multi-particulates A include members of the therapeutic categories such as analgesics, anti-inflammatory agents, anthelmintics, anti-arrhythmic agents, anti-bacterial agents, anti-viral agents, anticoagulants, anti-depressants, anti-diabetic agents, anti-epileptic agents, anti-fungal agents, anti-gout agents, anti-hypertensive agents, anti-malarial agents, anti-migraine agents, anti-muscarinic agents, anti-neoplastic agents, erectile dysfunction improving agents, immunosuppressants, anti-protozoa agents, anti-thyroid agents, anti-anxiolytic agents, sedatives, hypnotics, neuroleptics, β-blockers, cardiac inotropic agents, corticosteroids, diuretics, anti-Parkinsonian agents, gastrointestinal agents, histamine receptor antagonists, keratolytics, lipid regulating agents, anti-angina agents, cox-2 inhibitors, leucotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, nutritional oils, anti-benign prostate hypertrophy agents, essential fatty acids, non-essential fatty acids, and any combinations of two or more thereof.

In some embodiments, the APIs are selected from those commonly prescribed for relieving pain such as barbiturates and opioids. Representative examples include codeine, phenazocine, tilidine, tramadol, meperidine, sufentanil, prodine, methadone, pentazocine, oxycodone, oxymorphone, hydrocodone, hydromorphone, tapentadol, morphine, buprenorphine, and fentanyl (including derivatives thereof). Other drugs that can be misused for non-therapeutic purposes have hallucinogenic properties or otherwise affect the central nervous system, including stimulants such as amphetamines. Yet other examples of active pharmaceutical ingredients include alfentanil, allobarbital, allylprodine, alphaprodine, alprazolam, amfepramone, amphetamine, amphetaminil, amobarbital, anileridine, apocodeine, barbital, benzylmorphine, bezitramide, bromazepam, brotizolam, butobarbital, butorphanol, camazepam, chlorodiazepoxide, clobazam, clonazepam, clonitazene, clorazepate, clotiazepam, cloxazolam, cocaine, cyclobarbital, cyclorphan, cyprenorphine, delorazepam, desomorphine, dextromoramide, dextropropoxyphen, dezocine, diampromide, diamorphone, diazepam, dihydrocodeine, dihydromorphine, dimenoxadol, dimepheptanol, dimethylthiambutene, dioxaphetyl butyrate, dipipanone, dronabinol, eptazocine, estazolam, ethoheptazine, ethylmethylthiambutene, ethyl loflazepate, ethylmorphine, etonitazene, etorphine, fencamfamine, fenethylline, fenproporex, fludiazepam, flunitrazepam, flurazepam, halazepam, haloxazolam, heroin, hydroxypethidine, hydroxymethyl morphinane, isomethadone, ketazolam, ketobemidone, levomethadyl acetate, levomethadone, levorphanol, levophenacylmorphane, lofentanil, loprazolam, lorazepam, lormetazepam, mazindol, medazepam, mefenorex, meprobamate, meptazinol, metazocine, methylmorphine, methamphetamine, methaqualone, methylphenidate, methylphenobarbital, methyprylon, metopon, midazolam, modafinil, myrophine, nabilone, nalbuphine, nalorphine, narceine, nicomorphine, nimetazepam, nitrazepam, nordazepam, norlevorphanol, normethadone, normorphine, norpipanone, opium, oxazepam, oxazolam, pernoline, pentobarbital, pethidine, phenadoxone, phenomorphan, phenoperidine, piminodine, pholcodine, phenmetrazine, phenobarbital, phentermine, pinazepam, pipradrol, piritramide, prazepam, profadol, proheptazine, promedol, properidine, propoxyphene, remifentanil, secbutabarbital, secobarbital, temazepam, tetrazepam, triazolam, and vinylbital.

The pharmaceutically active agent is present in the formulation in an amount effective for the intended therapeutic purpose. These amounts are well known in the art. Indeed, all of the active agents embraced by the present invention are known per se, as are the doses at which they can be given safely and effectively for the intended therapeutic purpose. In some embodiments, the pharmaceutically active agent is present in an amount of about 5 wt % to about 50 wt % and in some other embodiments from about 15 wt % to about 35 wt %, based on the total weight of inner (or active) core.

Multiple-particulates "A" are made such that the API may be embedded in a polymer matrix such as a non-ionic pH-independent and/or a cationic pH-dependent polymer. Types of polymers that fall into either of these categories include (meth)acrylic polymers and (meth)acrylic copolymers (e.g., copolymers of alkyl (meth)acrylates and copolymers of alkylamino(meth)acrylates), quaternary ammonium (meth)acrylic polymers, and cellulose derivatives. Representative examples of pH-dependent polymers and nonionic pH-independent polymer are listed in Table 2.

TABLE 2

Exemplary Polymers to Form Matrix of Multi-particulates A

| Polymers | Trade Name/Supplier |
| --- | --- |
| Cationic copolymer based on dimethylaminoethyl methacrylate, butyl methacrylate, and methyl methacrylate (Cationic pH-dependent polymer) | EUDRAGIT ® E PO/Evonik |
| Copolymer of ethyl acrylate, methyl methacrylate and a low content of methacrylic acid ester with quaternary ammonium groups (Ammonium Methacrylate Copolymer, Type A, NF) (Non-ionic pH-independent polymer) | EUDRAGIT ® RL 100, RS100/Evonik |
| Copolymer of ethyl acrylate, methyl methacrylate and a low content of methacrylic acid ester with quaternary ammonium groups (Ammonio Methacrylate Copolymer, Type B, NF) (Non-ionic pH-independent polymer) | EUDRAGIT ® RS100/Evonik |
| Hydroxypropylcellulose (Non-ionic pH-independent polymer) | Klucel ™ E, L, J, G, M and H grades/Ashland |
| Hydroxypropyl methylcellulose (Non-ionic pH-independent polymer) | METHOCEL ™ E, F, J, and K/Dow Chemicals |
| Hydroxyethylcellulose (Non-ionic pH-independent polymer) | NATRASOL ™ L, G, M and H grades/Ashland |
| Ethylcellulose (Non-ionic pH-independent polymer) | ETHOCEL ™ 7FP, 10FP, 45FP and 100 FP/Dow Chemicals N7, N 10, N14, N22, N50 and N100 grades/Ashland |
| Cellulose Acetate Butyrate (Non-ionic pH-independent polymer) | CAB-381-0.5/Eastman |
| Cellulose Acetate (Non-ionic pH-independent polymer) | CA-398-3, CA-398-6, CA-398-10, CA-398-30/Eastman |

Exemplary pH-dependent polymer matrices include cationic pH-dependent release polymers that are soluble in gastric fluid (FIG. 1), but swell and become permeable at pHs above 5.0 (FIG. 2). In some embodiments, the cationic pH-dependent polymer matrix comprises EUDRAGIT® E PO which has a molecular weight about 47,000 and a glass transition temperature about 48° C. EUDRAGIT® E PO is soluble in gastric fluid up to pH 5.0; however, it is not soluble above pH 5.0, but is swellable and permeable above pH 5.0. As a result, EUDRAGIT® E PO will suddenly slow down release of drug into the intestinal fluid. Due to the uniqueness of its chemical properties, EUDRAGIT® E may act as an absorption retardant polymer when ingested in overdose quantities.

Yet other polymers that may be suitable for use as a matrix include the viscosity building polymers e.g., the hydrophilic polyethylene oxide polymers (that are disclosed herein below), alone and in combination with at least one other type of polymer disclosed herein.

The polymer matrix may be present in the multi-particulates A in a range of about 30 wt % to about 95 wt % and in other embodiments, from about 40 wt % to about 75 wt %, based on the total weight of the multi-particulates A.

The plasticizer may increase the elasticity of the polymer in multi-particulates A, which therefore makes multi-particulates A crush-resistant. The plasticizer may also act as an aversion agent. The plasticizer is soluble in both aqueous and non-aqueous solvents that are commonly used to extract opioids and other abuse-prone drugs from commercial formulations. As an aversion agent, the plasticizer acts as a tissue irritant that causes discomfort if administered in conjunction with an opioid or other abuse-prone active pharmaceutical ingredient with which it is co-extracted.

Suitable plasticizers include liquid esters, e.g., triethyl citrate, propylene glycol, polyethylene glycols, triacetin, diethylene glycol monoethyl ether, dibutyl sebacate and diethyl phthalate. In some embodiments, the dielectric constant values of the plasticizer are in a range of about 5 to about 60. In other embodiments, the dielectric constant values of the plasticizer are in a range of about 10 to about 40.

The plasticizer may be present in an amount that is sufficient to make multi-particulates A substantially crush-resistant, but not in quantities that negatively impact the dissolution of the API, and also result in discomfort to the abuser when the plasticizer is co-eluted with the API when administered in an non-prescribed way. In general, the plasticizer may be present in a range of about 0.1 wt % to about 20 wt %, and in some embodiments from about 2.0 wt % to about 10 wt %, based on the total weight of the multi-particulates A. The amount of plasticizer provides an adequate rubbery state and elongation property to the polymer to achieve crush-resistance, making it impossible to pulverize the multi-particulates A into fine powder, preventing abuser from snorting. The crush-resistance of the multi-particulates may be determined by a measurement of a breaking strength or resistance to breaking of the particulates using an Instron Tester or equivalent. In some embodiments, the resistance to breaking is not less than about 300 Newtons/m$^2$ (0.3 kPa).

Pharmaceutically acceptable surfactants that are useful in the practice of the present invention have solubility in oils, co-solvents, or aqueous media. The surfactant component helps in modulating the solubility of the compound as well in reducing the abuse potential by a dual mechanism. First, it elicits the irritant response when administered "as is" by nasal or injection routes, and second, by co-eluting with the drug when extracted with the commonly used solvents such as aqueous and organic solvents. Surfactants produce tissue irritation when applied to nasal mucosa and will cause local irritation at an injection site. Further, docusate sodium is commonly used as a stool softener/laxative, so while providing some relief for opioid-induced constipation at the intended dose, it can cause undesirable gastrointestinal effects if large quantities are ingested. Similar gastrointestinal effects can be obtained by ingesting other surfactants. The surfactant is present in an amount that results in discomfort to the abuser when the surfactant is co-eluted with the pharmaceutically active agent, as described herein. The HLB values of the surfactants are in a range of about 4 to about 30.

Types of surfactants that may be useful in the practice of the present invention include non-ionic surfactants e.g., esters of fatty acids, especially of C8-C24 and preferably of C16-C22, and fatty acid esters of polyols such as glycerol or sorbitol; sorbitan fatty acid esters ethoxylated with from 2 to 30 moles of ethylene oxide; polyethylene glycol fatty acid esters; polyethyleneglycol esters and polyethyleneglycol ethers; and polyethoxylated carboxylic acids (e.g., PEG-35 castor oil, PEG-40 castor oil, steareth-2 (Brij 72, Uniqema), steareth-21 (Brij 721, Uniqema), ceteareth-25 (Cremophor A25, BASF Cooperation), PEG-7 hydrogenated castor oil (Cremophor WO7, BASF Cooperation), and PEG-30 Dipolyhydroxystearate (Arlacel P 135, Uniqema)). Anionic surfactants e.g., alkyl ether sulfates and sulfosuccinates, may also be useful. Alternatively cationic and amphoteric surfactants such as phospholipids, lysophospholipids, and pegylated phospholipids may also be used.

Yet other surfactants that may be useful include vitamin E and derivatives thereof, e.g., PEGylated derivatives of vitamin E. Examples include tocopherol PEG succinate, tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate. (See, e.g., U.S. 20140271593.)

The surfactant may be present in a range of about 0.1 wt % to about 20 wt %, and in some embodiments from about 2.0 wt % to about 10 wt %, based on the total weight of the multi-particulates A. Some representative surfactants are listed in Table 3.

TABLE 3

Representative Surfactants

| Surfactant | Trade Name/Supplier |
| --- | --- |
| Dioctyl sodium sulfosuccinate (docusate sodium) | Many names and suppliers |
| Sodium lauryl sufate | Many names and suppliers |
| PEG-32 glyceryl laurate | GELUCIRE ® 44/14/Gattefosse ACCONON ® C-44/Abitec |
| PEG-32 glyceryl palmitostearate | GELUCIRE ® 50/13/Gattefosse |
| PEG-35 castor oil (polyoxyl 35 ricinoleate castor oil) | CREMOPHOR ® EL/BASF ETOCAS ® 35 NF/Croda |
| PEG-8 glyceryl caprylate/caprate | LABRASOL ®/Gattefosse ACCONON ® MC-8/Abitec |
| PEG-6 glyceryl caprylate/caprate | SOFTIGEN ® 767/Sasol ACCONON ® CC-6/Abitec |
| PEG-40 hydrogenated castor oil (PEG-40 hydrogenated ricinoleate) | CREMOPHOR ® RH 40/BASF |
| Macrogol 15 hydroxystearate (polyoxyl 15 hydroxystearate) | SOLUTOL ® HS15/BASF |
| Block copolymers based on ethylene oxide and propylene oxide | PLURONIC ® (e.g., 188 or 407)/BASF |
| Polyoxyethylene 20 sorbitan monolaurate (polysorbate 20) | TWEEN ® 20/ICI Americas |
| Polyoxyethylene 20 sorbitan monooleate (polysorbate 80) | TWEEN ® 80/ICI Americas |
| Sorbitan monolaurate | SPAN ® 20/Croda |
| Sorbitan monooleate | SPAN ® 40/Croda |
| Tocopherol PEG succinate (vitamin E TPGS) | Many names and suppliers |
| Polyoxyl 40 stearate | MYRJ ® 52/Croda |

Abuse-deterrence effects of certain combinations of aversion agents (e.g., plasticizer and surfactant) in a formulation are summarized in Table 4.

TABLE 4

Examples of Combinations of Aversion Agents

| Combination | Solubility | | Abuse Deterrence | |
| --- | --- | --- | --- | --- |
| | Water | Solvents | Injection | Nasal |
| Triethyl citrate + docusate sodium | Yes | Yes | Yes | Yes |
| Propylene glycol + docusate sodium | Yes | Yes | Yes | Yes |
| PEG-400 + docusate sodium | Yes | Yes | Yes | Yes |
| PEG-400 + PEG-40 hydrogenated castor oil | Yes | Yes | Yes | Yes |

The multi-particulates A are coated with a cationic pH-dependent polymer, also referred to herein as a functional membrane coating. It is believed that coating multi-particulates A with a cationic pH-dependent polymer enables the pH-dependent release of the API. In some embodiments, the cationic pH-dependent polymer is an amino methacrylate copolymer, e.g., a fully polymerized cationic copolymer of (2-dimethylaminoethyl) methacrylate, butyl methacrylate, and methyl methacrylate in a 2:1:1 ratio.

The amount of the cationic pH-dependent polymer present in the functional coat applied onto multi-particulates A may be in a range of about 20 wt % to about 80 wt %, and in some embodiments from about 25 wt % to about 50 wt %, based on the total weight of the functional coating composition. In some embodiments, the functional coating composition may also include a non-ionic pH-independent polymer, which may be the same or different from the non-ionic pH-independent polymer that may be present in the matrix, an anti-tacking agent (e.g., talc and magnesium trisilicate) and/or a plasticizer, which may be the same or different from the plasticizer that is elsewhere present in multi-particulates A. The amount of the non-ionic pH-independent polymer present in the functional coat applied onto multi-particulates A may be in a range of about 20 wt % to about 80 wt %, and in some embodiments from about 40 wt % to about 70 wt %, based on the total weight of the functional coating composition.

In some embodiments, multi-particulates A may further include an intermediate coating layer, also referred to herein as a seal coating layer, disposed between the polymer matrix, e.g., the inner core, and the outer coating layer. The intermediate coating layer includes a non-ionic pH-independent polymer, which may be the same or different from the non-ionic pH-independent polymer that may be included in the polymer matrix described hereinabove. In some embodiments, the non-ionic pH-independent polymer that is included in the intermediate coating layer is a cellulose ether, e.g., a water-soluble methylcellulose and hydroxypropylmethylcellulose polymer. The amount of the polymer ranges from about 40 wt % to about 100 wt %, and in some embodiments from about 70 wt % to about 95 wt %, based on the total weight of the intermediate seal coating composition. In some embodiments, the seal coating composition may also include an anti-tacking agent (e.g., talc and magnesium trisilicate) and a plasticizer, which may be the same or different from the other anti-tacking agent that may be present and the plasticizer that is present in multi-particulates A. As disclosed herein, the intermediate coating composition may also include an amount of the drug, which may be therapeutically effective in and of itself, as well as the plasticizer and/or the surfactant, as well as other ingredients such as one or more solvents (both aqueous and organic, e.g., ethanol), as well as other excipients (disclosed herein below) that may also be included in the composition.

Method of Manufacture of Multi-Particulates A

Multi-particulates A may be prepared in several ways, including hot melt extrusion (HME) and film melt. In hot melt extrusion, a thermoplastic carrier polymer (e.g., non-ionic pH-independent and/or cationic pH-dependent polymer) is combined with an active pharmaceutical ingredient, a plasticizer, a surfactant, as well as any optional ingredients, e.g., an ion exchange polymer, alkaline buffering agent, and viscosity-building agent, to form a powdery mixture. The mixture is introduced into one or two rotating screws that convey the powder into a heated zone where shear forces compound the materials until a molten mass is achieved. Hot-melt extrusion equipment typically includes an extruder, auxiliary equipment for the extruder, downstream processing equipment, and other monitoring tools used for performance and product quality evaluation. The extruder is typically composed of a feeding hopper, barrels, single or twin screws, and the die and screw-driving unit. The auxiliary equipment for the extruder mainly includes a heating/cooling device for the barrels, a conveyer belt to cool down the product and a solvent delivery pump. The monitoring devices on the equipment include temperature gauges, a screw-speed controller, an extrusion torque monitor and pressure gauges.

The utilization of different shaped dies and appropriate downstream processing makes hot-melt extrusion a highly versatile technology for the manufacture of a vast number of different dosage forms. Extrudates can be produced by extruding the material through round-shaped dies onto cooled rolls. Extruded strands are cut into short cylinders. Cutting is performed after cooling of the strand on conveyer belts.

The sizes of multi-particulates A are significantly large enough to prevent the multi-particulates from being snorted. In some embodiments, grinding of the hot-melt extrudates yields multi-particulates A with a mean size distribution from about 100 microns to about 1000 microns, and in some embodiments from about 250 microns to 750 microns (as measured by weight frequency distribution using sieving method).

Composition of Multi-Particulate B

Figure 3A:
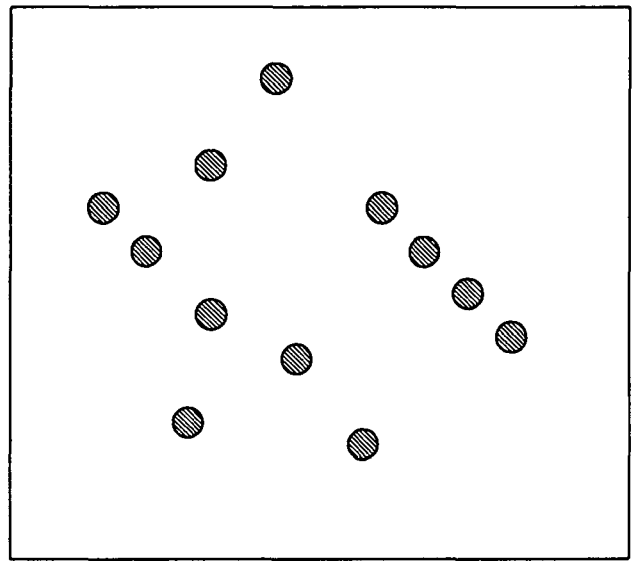
FIGS. 3A and B are schematic diagrams showing dispersion of multi-particulate A in the GI tract, wherein (A) shows a one unit dose wherein the surface area of the multi-particulate is completely exposed to the fluid thus providing faster API release and a lower micro-environmental viscosity due to less quantity of the viscosity-building polymer, and (B) shows a multiple unit dose, wherein the multi-particulates are entrapped in the hydrated viscosity-building polymer, thus diminishing surface area of the multi-particulates that are exposed to the GI fluid, thereby lowering drug release, and wherein a drastic increase in pH to about at least 6 enhances the gelling effect, thereby suppressing the dissolution rate of the API through the Eudragit E, and wherein there is a substantial increase in micro-environmental viscosity due to larger quantities of the viscosity-building polymer present in the multiple unit dose.
Figure 3B:
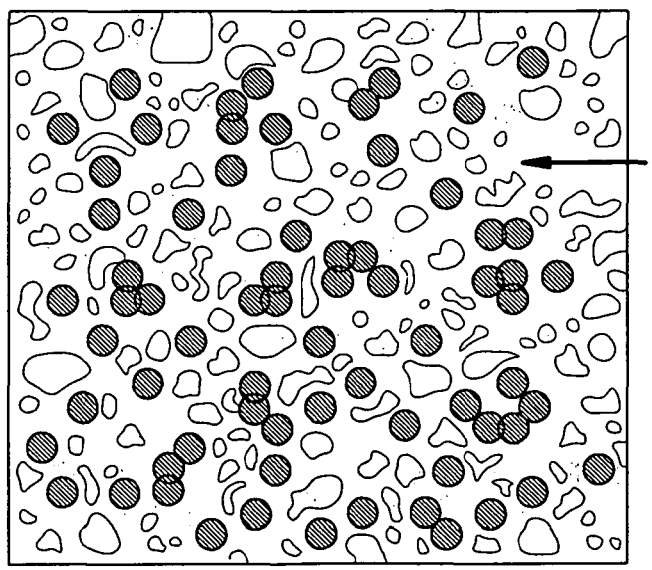
Figure 4:
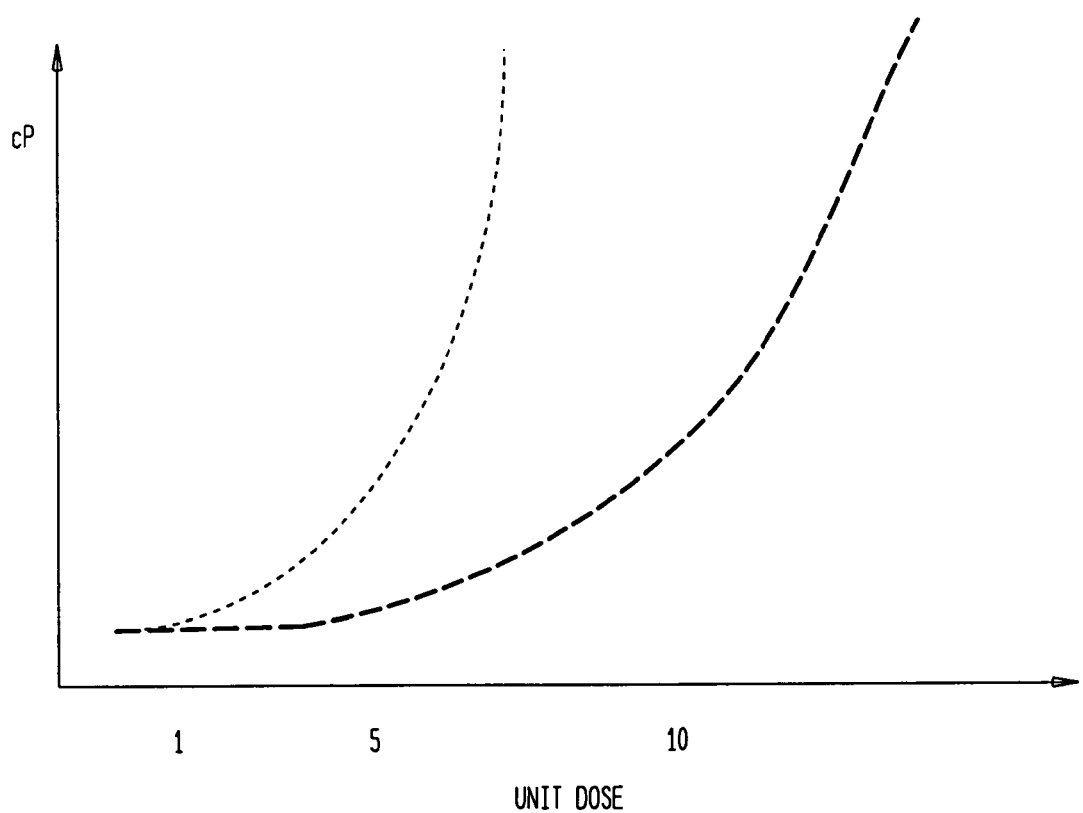
FIG. 4 is a prophetic graph showing the rheology profile of a viscosity building polymer in a formulation when taken in increasing doses (viscosity on y-axis, number of doses on x-axis).
Figure 5:
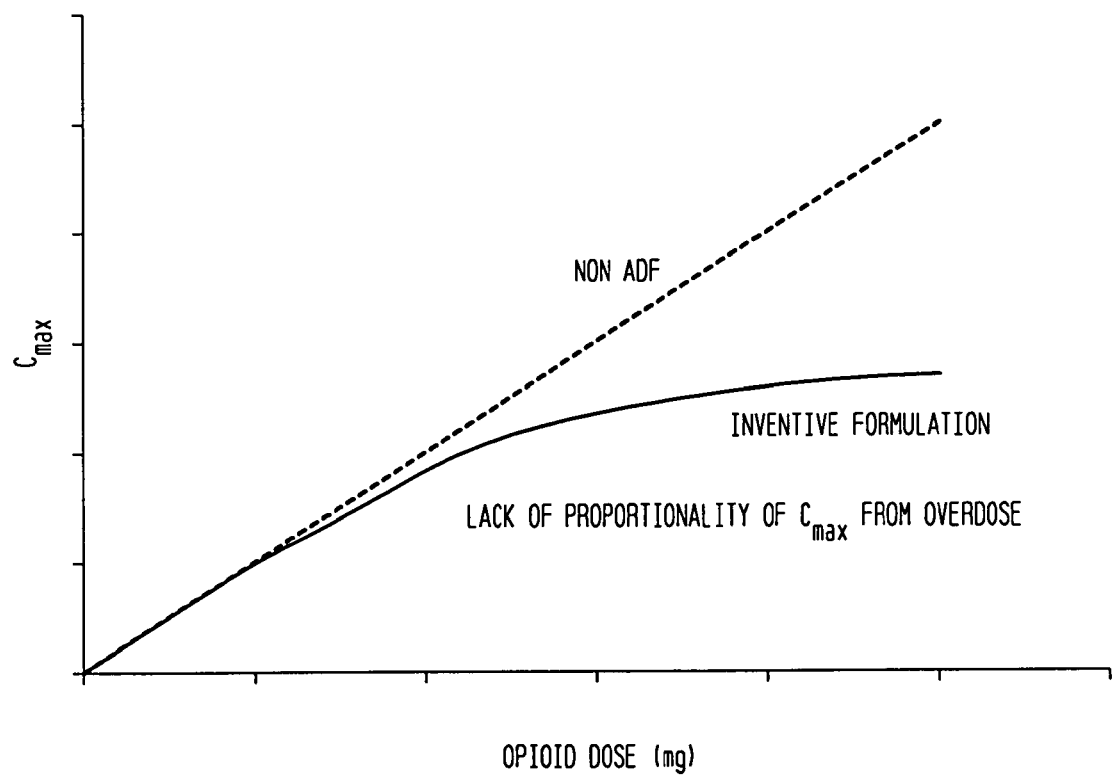
FIG. 5 is a prophetic graph showing $C_{max}$ vs opioid dose (Non-Abuse-Resistant formulation vs. inventive Formulation), and the lack of proportionality of $C_{max}$ from the overdose, and which shows overdose protection.

Multi-particulates B contain a viscosity-building polymer. A "viscosity-building polymer" as used herein increases the viscosity of a solution if the formulation is tampered with. That is, the viscosity-building polymer increases the viscosity in the GI tract if multiple doses of an API are taken by a patient and/or prevents syringeability if the formulation is extracted into aqueous media. The viscosity-building polymer is present in an amount that does not retard the release of the API from a single dose administration, but does slow down the API release after multiple-unit doses are taken (e.g., as illustrated in FIGS. 3 and 4). As the viscosity of the solution (resulting from the contact of the formulation with the aqueous gastric fluid) increases, the API becomes entrapped in the polymer gel matrix and does not exhibit immediate-release properties but rather extended-release properties. It is believed that the ingestion of multiple doses will not proportionally increase the maximum concentration ($C_{max}$) of the API to reach the full potential of addictive effects (e.g., euphoria, sedation, and/or relaxation) of the API (as illustrated in FIG. 5). In addition, it will take a longer time to reach maximum concentration ($t_{max}$). The results will include a reduced desire to deliberately overdose on the API.

In some embodiments, the viscosity-building polymer is a high-molecular weight polymer. In other embodiments, the viscosity-building polymer is a hydrophilic polymer. Certain hydrophilic polymers, such as polyethylene oxides, form viscous gels upon contact with aqueous media and will not have adequate "syringeability" to permit injection. Examples of useful polyethylene oxide polymers that are sold as POLYOX® by The Dow Chemical Co. are listed in Table 4 below (wherein the superscripts a, b and c refer to 5%, 2% and 1% solutions, respectively, measured at 25° C. using a Brookfield viscometer in accordance with the manufacturer's instructions).

TABLE 4

Representative Viscosity-building Polymer

| Trade Name | INCI Name | Approx. Molecular Weight | Viscosity (mPa · s) |
|---|---|---|---|
| POLYOX ® WSR-205 | PEG-14M | 600,000 | about 4500-about 8800$^a$ |
| POLYOX ® WSR-301 | PEG-90M | 4,000,000 | about 1650-about 5500$^c$ |
| POLYOX ® WSR N-10 | PEG-2M | 100,000 | about 12-about 50$^a$ |
| POLYOX ® WSR N-80 | PEG-5M | 200,000 | about 65-about 115$^a$ |
| POLYOX ® WSR N-750 | PEG-7M | 300,000 | about 600-about 1,000$^a$ |
| POLYOX ® WSR N-3000 | PEG-14M | 400,000 | about 2250-about 4500$^a$ |
| POLYOX ® WSR N-12K | PEG-23M | 1,000,000 | about 400-about 800$^b$ |
| POLYOX ® WSR N-60K | PEG-45M | 2,000,000 | about 200-about 400$^b$ |

Other useful viscosity-building polymers include pectin, polysaccharides such as pectin, crosslinked starches, and cellulose derivatives such as sodium carboxymethycellulose, silicone polymers, carbomers (such as Carbopol 934P NF, Carbopol 974P NF and Carbopol 971P NF, available from Noveon Pharmaceuticals), polycarbophil tragacanth, and gums such as xanthan gum.

The viscosity-building polymer is present in an amount that will not impact the viscosity of the solution (formed in the GI tract) if the prescribed dose of API is taken, but is sufficient to increase the viscosity of the solution in the GI tract if multiple doses of the API are taken by a patient. The result is viscosity-building when the polymer is exposed to aqueous media, which prevents a user from injecting the formulation using a hypodermic needle. The viscosity-building polymer may be present in an amount of about 75 wt % to about 100 wt %, and in some embodiments from about 80 wt % to about 95 wt %, based on the total amount of the multi-particulates B.

The hydrodynamic volume and swelling capacity of anionic polymers, such as carbomers, increase sharply when the carboxylic groups become ionized at a pH of about 6. The highest plateau in viscosity may be achieved in a pH range of about 6 to about 7. Therefore, buffering agents or alkalizing agents can also be used to enhance the viscosity-building effect of carbomers with good buffering capacity which contributes to maintenance of the desired pH and provides high viscosity at low concentrations of polymer. Examples of carbomer buffering agents include sodium carbonate, sodium bicarbonate, potassium dibasic phosphate, sodium dibasic phosphate or mixtures thereof. In some embodiments, the carbomer buffering agents may be present in a range of about 0.005 g/g (or 0.5% w/w to about 0.1 g/g (or 10%/w/w), based on the total weight of the of the viscosity building polymer present in multi-particulate B.

Figure 6:
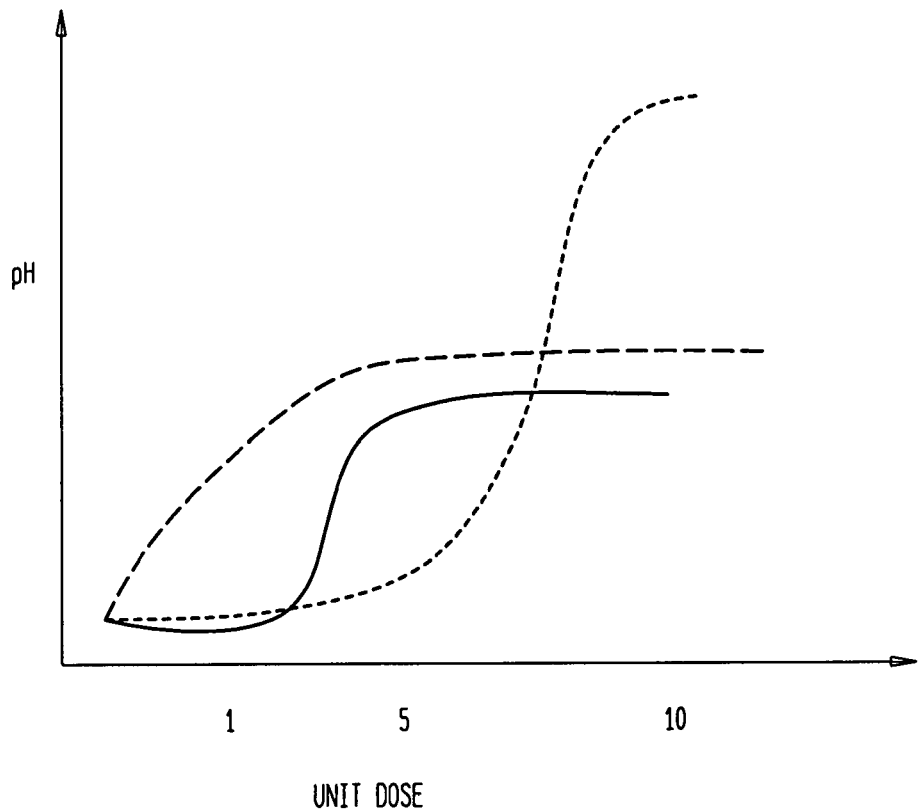
FIG. 6 is a prophetic graph showing increase in pH of gastric fluid with multiple doses (pH on y-axis, number of doses on x-axis).

Multi-particulates B also include an alkaline buffering agent, which as used herein is a weak base that maintains the pH of a solution near a chosen value. The alkaline buffering agent also functions to increase the pH of the gastric acid in the stomach if multiple doses of the API are taken by a patient. The increase in pH of the gastric acid in the stomach will prevent the cationic pH-dependent polymer from releasing the API from multi-particulates A. Increasing gastric fluid pH to a pH of about greater than 5 retards dissolution of the API by causing the cationic pH-dependent polymer present in the matrix or the functional membrane coat to become insoluble and swell if excess doses are ingested (FIG. 6). The swollen pH-dependent polymer will be permeable to the drug, allowing the API to slowly diffuse from the swollen polymer over an extended period of time and diminishing or eliminating the euphoric effect associated with overdoses.

Representative examples of alkaline buffering agents include amino acids, alkaline metal salts of amino acids, aluminum hydroxide, aluminum hydroxide/magnesium carbonate/calcium carbonate co-precipitate, aluminum magnesium hydroxide, aluminum hydroxide/magnesium hydroxide co-precipitate, aluminum hydroxide/sodium bicarbonate coprecipitate, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tefrasodium pyrophosphate, tripotassium phosphate, trisodium phosphate, frometamol, and mixtures thereof.

The alkaline buffering agent may be present in an amount that will not impact the pH of the gastric fluid if one unit dose of API is administered but is sufficient to increase the pH of the gastric fluid in the stomach to prevent the immediate-release of the API from the multi-particulates A when more than the prescribed dose of the API is administered. In some embodiments, the alkaline buffering agent in multi-particulates B will increase the pH of the gastric fluid from about a pH of 1 to about 5. The alkaline buffering agent is generally present in the amount of about 0.1 wt % to about 25 wt %, and in some embodiments from about 1 wt % to about 15 wt %, based on the total weight of the multi-particulates B.

In some embodiments, multi-particulates B may be coated with non-ionic pH-independent and/or cationic pH-dependent polymer as disclosed herein.

Method of Manufacture of Multi-Particulate B:

Multi-particulate B may be prepared in several ways, including hot-melt extrusion, dry granulation (e.g., direct blend, roller compaction) or wet granulation processes to allow an intimate mix of a viscosity building polymer and an alkaline buffering agent to promote a rapid gelling effect of the granulated polymer when exposed to gastrointestinal fluid. The granulations obtained may be milled to achieve uniform granules. In some embodiments, the mean particle size distribution of multi-particulates B is about 100 microns to about 1000 microns; and in other embodiments, from about 250 microns to about 750 microns (as measured in accordance with the techniques disclosed herein for multi-particulates A).

Optional Ingredients

The oral pharmaceutical compositions of the present invention may further include additional, i.e., optional, ingredients. Generally, these ingredients may be included in the composition in various ways. For example, they may be included as additional ingredients in either the first (A) or second (B) populations of multi-particulates. In some embodiments, the optional ingredient may be present in the composition in the form of a separate population of micro-particulates (together with one or more ingredients disclosed herein) or in yet other embodiments, they may be present as extra-granular components.

In some embodiments, the compositions may include a disintegrant. Useful disintegrants include carmellose calcium, carboxymethyl starch sodium, croscarmellose sodium, crospovidone (crosslinked homopolymer of N-vinyl-2-pyrrolidone), and low-substituted hydroxypropyl celluloses. Other useful disintegrants include sodium starch glycolate, colloidal silicon dioxide, alginic acid and alginates, acrylic acid derivatives, and various starches. In some embodiments, the disintegrant may be present in the composition as a further population of multi-particulates (which are described in Example III as "type C granules"). The disintegrant may be present in an amount ranging from about 0.5 wt % to about 5 wt %, and in some embodiments from about 1.0 wt % to about 4 wt %, based on the total weight of the multi-particulate composition. In some embodiments, the disintegrant may be formulated into multi-particulates along with at least one other excipient including a diluent, alkaline buffering agent (which may be the same or different from the alkaline buffering agent contained in multi-particulates B) and/or a gelling agent (e.g., alginic acid, calcium alginate and xanthan gum). In such embodiments, the diluent may be present in an amount of about 1 wt % to about 25 wt % and in some other embodiments from about 2 wt % to about 10 wt %, based on the total weight of the multi-particulate composition; the alkaline buffering agent may be present in an amount of about 0.1 wt % to about 95 wt % and in some other embodiments from about 50 wt % to about 85 wt %, based on the total weight of the multi-particulate composition; and the gelling agent may be present in an amount of about 0.1 wt % to about 10 wt % and in some other embodiments from about 4.0 wt % to about 8.0 wt %, based on the total weight of the multi-particulate composition.

In some embodiments, the composition may further include a second viscosity building polymer, which may be the same or different from the viscosity building polymer contained in the second population of multi-particulates (B). The second viscosity building polymer is preferably present as a separate population of multi-particulates, which may include additional ingredients such as a plasticizer (which may also be the same or different from the plasticizer contained in multi-particulates A and/or B). The second viscosity building polymer may be present in an amount of about 75 wt % to about 100 wt %, and in some embodiments from about 85 wt % to about 99 wt %, based on the total weight of the multi-particulate composition. The plasticizer may be present in an amount of about 0.1 wt % to about 24.5 wt %, and in some embodiments from about 5.0 wt % to about 20 wt %, based on the total weight of the multi-particulate composition.

In some embodiments, the compositions further include an ion exchange polymer (e.g., Amberlite™ IRP64 and Amberlite™ IRP69). These polymers may be present in multi-particulates A or B, a separate population of multi-particulates, or be present in extra-granular form. The ion exchange polymers are believed to form a matrix or complex with the drug and thus may alter the release of the drug. Thus, in these embodiments, the composition may exhibit an extended release profile. The ion exchange polymer also sequesters the active pharmaceutical ingredient by binding to the API when an excessive amount of the drug is consumed. The ion exchange polymer may be present in a concentration of about 1-5 M, and in some embodiments from about 1-3 M, based on the total molarity of the drug susceptible to abuse.

In some embodiments, the compositions further contain an acid suppressing agent, such as an H2-blocker or a proton pump inhibitor (PPI). The acid suppression agent is present in an amount that when the formulation is taken in the prescribed amount, it does not suppress gastric acid secretion or increase the pH of the gastric fluid but does raise the pH of the gastric fluid when multiple dosage units are taken. The transient rise in pH of the gastric fluid suppresses the dissolution rate of the cationic pH-dependent polymer present in multi-particulates A, which in turn suppresses the API release.

H2-blockers competitively inhibit histamine at the H2 receptors which leads to a reduction in secretion of gastric acid. Representative H2-blockers include ranitidine, famotidine and cimetidine.

Proton pump inhibitors reduce the production of acid by blocking the enzyme in the wall of the stomach that produces acid, thereby raising the pH of the stomach. Representative proton-pump inhibitors include omeprazole, lansoprazole, esomeprazole, pantoprazole and rabeprazole.

The acid-suppressing agent is present in the formulation in an amount that will maintain a normal gastric fluid pH (1-2) when the prescribed dosage is taken under fasting conditions, but will cause a rapid rise in gastric fluid pH to about greater than 5, when multiple doses are taken. The effect is the delay in the release of the active pharmaceutical ingredient from multi-particulates A. The presence of acid suppressing agent enhances the binding of the API to the ion exchange polymer.

In some embodiments, wherein the drug or API is an opioid, the compositions may further include an opioid antagonist. Opioid antagonists prevent IV or nasal abuse of APIs that are opioids. They are not absorbed and have minimal oral absorption; therefore, they do not exert an antagonist effect when taken orally. However, if the enhanced abuse deterrent formulation is either crushed and then injected IV or IM, or is grinded and then inhaled, the opioid antagonist will be directly introduced into the systemic circulation where it will antagonize the effects of the opioid. When taken by mouth, the opioid antagonists are metabolized in the liver, so that peripheral antagonism of opioids exists in the gut, but after metabolism little opioid antagonists passes into the central nervous system. The opioid antagonist may be present as a separate population of multi-particulates, further included with multi-particulates A or B, or extra-granularly.

Representative examples of opioid antagonists include naloxone, naltrexone, nalmefene, nalid, nalmexone, nalorphine and naluphine and a corresponding physiologically acceptable compound. The opioid antagonist may be present in a weight ratio of about 0.01:1 to about 1:1 to the total weight of the opioid drug present in the composition.

In some embodiments, the compositions may include a glidant which improves the flow of powder blends, pellets, etc. and minimizes dosage form weight variations. Useful glidants include fumed or colloidal silica, talc, kaolin, or a combination of two or more thereof. Different grades of fumed silica are commercially available from various sources, including the CAB-O-SIL® products sold by Cabot Corporation and the AEROSIL® products sold by Evonik Industries.

In some embodiments, the compositions may include a diluent or filler. Useful fillers or diluents include starches, lactose, cellulose derivatives, confectioner's sugar and the like. Different grades of lactose include lactose monohydrate, lactose DT (direct tableting), lactose anhydrous, and others. Different starches include maize starch, potato starch, rice starch, wheat starch, pregelatinized starch, and others. Different celluloses that can be used include crystalline celluloses, such as microcrystalline cellulose, and powdered celluloses. Other useful diluents include carmellose, sugar alcohols such as mannitol, sorbitol, and xylitol, calcium carbonate, magnesium carbonate, dibasic calcium phosphate, and tribasic calcium phosphate.

In some embodiments, the compositions may include a binder. Useful binders include hydroxypropyl celluloses in various grades, hydroxypropyl methylcelluloses in various grades, polyvinylpyrrolidones in various grades, copovidones, powdered acacia, gelatin, guar gum, carbomers, methylcelluloses, polymethacrylates, and starches.

In some embodiments, the compositions may include a lubricant. Useful lubricants include magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof.

In some embodiments, the compositions may include a sweetener. Useful sweeteners include sucrose, sucralose, and aspartame.

In some embodiments, the compositions may include a flavoring agent. Useful flavoring agents include pharmaceutically acceptable natural oils, natural flavors, and artificial flavors. Representative flavors include menthol, peppermint, wintergreen, orange, cherry, and other fruits, vanilla, almond and other nuts, etc. Mixtures of two or more flavoring agents may be advantageous.

In some embodiments, the compositions may include a coloring agent. Coloring agents can be used to color code compositions, for example, to indicate the type and dosage of the therapeutic agent therein. Coloring agents can also be used to differentiate the varied fractions of multi-particulates contained in a unit dosage form such as a capsule. Suitable coloring agents include natural and/or artificial colorants such as FD&C coloring agents, natural juice concentrates, pigments such as titanium dioxide, silicon dioxide, iron oxides, zinc oxide, and the like.

In some embodiments, the compositions may include a solvent. Useful solvents that can be used in processes of preparing pharmaceutical formulations of the present disclosure include water, methanol, ethanol, acetone, diacetone, polyols, polyethers, oils, esters, alkyl ketones, methylene chloride, isopropyl alcohol, butyl alcohol, methyl acetate, ethyl acetate, isopropyl acetate, castor oil, ethylene glycol monoethyl ether, diethylene glycol monobutyl ether, diethylene glycol monoethyl ether, dimethylsulfoxide, N,N-dimethylformamide, tetrahydrofuran, and mixtures of two or more thereof.

In some embodiments, compositions of the present application may contain an antioxidant which enhances the stability of a drug. The antioxidant may be present either as a part of a formulation or as a packaging component. Antioxidants can be present in amounts effective to retard decomposition of a drug that is susceptible to oxidation. The content of an antioxidant in the formulations generally ranges from about 0.001 to 10 weight %, with respect to the amount of the drug. Representative examples of antioxidants include ascorbic acid and its salts, tocopherols, sulfite salts such as sodium metabisulfite or sodium sulfite, sodium sulfide, butylated hydroxyanisole, butylated hydroxytoluene, ascorbyl palmitate, and propyl gallate. In embodiments wherein the anti-oxidant is included in a multi-particulate population, it may be present in an amount of about 0.001 wt % to about 0.5 wt %, and in some embodiments from about 0.002 wt % to about 0.25 wt %, based on the total weight of the multi-particulate population.

Some analgesic drugs, such as acetaminophen, ibuprofen, naproxen, diclofenac are commonly used in combination with opioids. Thus, in these embodiments, the compositions may further include an analgesic. These analgesic drugs may be present typically in a range of about 0.1 g/g (or 10% w/w) to about 0.50 g/g (or 50% w/w). In some embodiments, the analgesic is contained in a composition formulated as a tablet.

The pharmaceutical excipients disclosed herein are not intended to be exhaustive but are merely representative of the types of these ingredients that may be suitable for use in the present invention. Also, when a particular product and supplier is mentioned, in many cases similar products are available commercially from other suppliers and also can be used.

Method of Manufacture of Inventive Formulation

The solid pharmaceutical compositions may be prepared by mixing together multi-particulates A, multi-particulates B, and any additional additives, and compressed into a tablet or an orally disintegrating tablet (ODT), or loaded into a capsule.

The order in which the ingredients are mixed is not critical. In some embodiments, multi-particulates A are blended with multi-particulates B, and optionally any further populations of multi-particulates and/or extra-granular excipient(s) to make a final dosage form, e.g., a tablet of a hard or soft gelatin capsule. In some embodiments, the ratio of multi-particulates A to multi-particulates B is in the range of about 100:1 to about 1:100. In some embodiments, the ratio of multi-particulates A to multi-particulates B is in the range of about 10:1 to about 1:10. In some embodiments, the ratio of multi-particulates A to multi-particulates B is about 1:1.

In some embodiments, the amount of multi-particulates A is present in the composition in an amount of about 10-60%, and in some embodiments 20-50%, based upon the total weight of the compositions. In some embodiments, the amount of multi-particulates B is present in the composition in an amount of about 40-90%, and in some embodiments 50-80%, based upon the total weight of the compositions. Further, the total amount of alkaline buffering agent(s) present in the composition may vary from about 10 to about 50%, and in some embodiments about 20 to about 40%, based upon the total weight of the composition. The total amount of plasticizer(s) present in the composition may vary from about 5 to about 40%, and in some embodiments about 10 to about 30%, based upon the total weight of the composition. The total amount of viscosity building polymer (s) present in the composition may vary from about 30 to about 80%, and in some embodiments about 40 to about 70%, based upon the total weight of the composition.

The following examples further describe the invention but should not be construed as limiting the scope of the invention in any manner.

Example I

Formulations are prepared, using the ingredients listed in table 5 below.

TABLE 5

| Ingredient | mg/tablet A | mg/tablet B |
|---|---|---|
| Multi-particulates A | | |
| Oxycodone hydrochloride (Pharmaceutically Active Agent) | 40 | — |
| Oxymorphone hydrochloride (Pharmaceutically Active Agent) | — | 40 |
| Eudragit ® EPO (Cationic pH-dependent Polymer Matrix) | 80 | 80 |
| Triethyl citrate (Plasticizer; Aversion Agent) | 8 | 8 |
| Dioctyl sodium sulfosuccinate (Surfactant; Aversion Agent) | 3 | 3 |
| Colloidal silicon dioxide†(Glidant) | 0.75 | 0.75 |
| Multi-Particulates B | | |
| Carbomer ® 934 P (Viscosity-Building Polymer) | 10 | 10 |
| Sodium Bicarbonate (Alkaline Buffering Agent) | 10 | 10 |
| Extra-granular Excipients | | |
| Microcrystalline cellulose (tablet Diluent) | 50 | 50 |
| Crospovidone§(Disintegrant) | 12 | 12 |
| Colloidal silicon dioxide†(Glidant) | 0.75 | 0.75 |
| Magnesium Stearate (Lubricant) | 1.5 | 1.5 |

\* e.g., EUDRAGIT ® E PO, a product of Evonik Industries.
†e.g., AEROSIL ® 200, a product of Evonik
‡ e.g., POLYOX ® WSR-301, a product of the Dow Chemical Company.
§e.g., POLYPLASDONE ® XL, a product of Ashland Inc.

Formulation Procedure:

Preparation of Multi-Particulates A 1.1 Mix the active pharmaceutical ingredient, Eudragit® E PO, triethyl citrate, dioctyl sodium sulfosuccinate, and the first portion of colloidal silica in a high-shear mixer for 5 minutes.

1.2 Pass the mixture through a twin-screw hot melt extruder.

1.3. After cooling the extruded material, reduce particle sizes with a FitzMill® comminutor.

Preparation of Multi-Particulates B 2.1. Mix Carbomer® 934 P and Sodium Bicarbonate in a high shear granulator for 5 minutes.

2.2. Pass the powder mix from Step 2.1 to a roller compactor to form compacted ribbons.

2.3. Mill the ribbons from Step 2.2 using a FitzMill®

3. Blend the multi-particulates A from Step 1.3 with Multi-particulates B from Step 2.3, crospovidone, portion of colloidal silica in a V-blender for 15 minutes.

4. Add magnesium stearate to the blend from Step 3 and mix for 5 minutes.

5. Compress the blend from Step 4 into tablets.

Example II

Formulations are prepared, using the ingredients listed in table 6 below.

TABLE 6

| Ingredient | mg/tablet |
|---|---|
| Membrane-Coated Multi-particulates A | |
| CORE | |
| Oxycodone hydrochloride (Pharmaceutically Active Agent) | 40 |
| Eudragit ® EPO (Cationic pH-dependent Polymer matrix) | 80 |
| Triethyl citrate (Plasticizer; Aversion Agent) | 8 |
| Polyoxyl 40 hydrogenated castor oil\*\* (Surfactant; Aversion Agent) | 8 |
| Colloidal silicon dioxide†(Glidant) | 0.75 |
| FUNCTIONAL MEMBRANE-COATING | |
| Eudragit ® EPO (Cationic pH-dependent Functional Membrane-Coating Polymer) | 17 |
| Sodium Lauryl Sulfate (Emulsifier) | 1.7 |
| Stearic acid (Anti-tacking agent) | 2.6 |
| Talc (Anti-tacking agent) | 8.6 |
| Multi-Particulates B | |
| Carbomer ® 974P (Viscosity-building polymer) | 10 |
| PEG-90M‡ (Viscosity-building polymer) | 10 |
| Sodium Bicarbonate (Alkaline Buffering Agent) | 10 |
| Multi-Particulates C | |
| Omeprazole(Proton Pump Inhibitor) | 5 |
| Sodium bicarbonate(alkaline buffering agent) | 5 |
| Extra-granular Excipients | |
| Microcrystalline Cellulose (Tablet Diluent) | 75 |
| Crospovidone§(Disintegrant) | 12 |
| Colloidal silicon dioxide†(Glidant) | 0.75 |
| Magnesium Stearate (Lubricant) | 1.5 |

\* e.g., EUDRAGIT ® E PO, a product of Evonik Industries.
\*\*e.g., CREMOPHOR ® RH 40, a product of BASF.
†e.g., AEROSIL ® 200, a product of Evonik
‡e.g., POLYOX ® WSR-301, a product of the Dow Chemical Company.
§e.g., POLYPLASDONE ® XL, a product of Ashland Inc.

Formulation Procedure:

1. Preparation of Membrane-Coated Multi-Particulates A
   1.1. Preparation of the Polymer Matrix
      1.1.1. Mix the drug, Eudragit® E PO, triethyl citrate, polyoxyl 40 hydrogenated castor oil, a portion of colloidal silica in a high-shear mixer for 5 minutes.
      1.1.2. Pass the mixture through a twin-screw hot melt extruder.
      1.1.3. After cooling the extruded material, reduce particle sizes with a FitzMill® comminutor.
   1.2. Functional Membrane Coating
      1.2.1. Dissolve sodium lauryl sulphate in purified water, and slowly add Eudragit® E PO into the solution while mixing. Continue mixing for at least 1-hr.

1.2.2. Add stearic acid and talc to the dispersion from Step 1.2.1 while mixing. Continue mixing for at least 1-hr.
1.2.3. Warm the multi-particulates A in a Wurster® fluid bed coater with an inlet air temperature of 50°-60° C. and sufficient air volume for fluidization of the multi-particulates.
1.2.4. When the product temperature is reached to 35° to 40° C., start spraying the dispersion from Step 1.2.3 onto multi-particulates while maintaining an inlet air temperature of 50°-60° C. and sufficient air volume for the fluidization until the target coating weight gain is reached.
1.2.5. Dry the multi-particulates from Step 1.2.4.
2. Preparation of Multi-Particulates B
    2.1. Mix Carbomer® 974 P. PEG-90M and Sodium Bicarbonate in a high shear granulator for 5 minutes.
    2.2. Densify the powder mix from Step 2.1 using a roller compactor by forming compacted ribbons
    2.3. Mill the ribbons from Step 2.2 using a FitzMill®
3. Preparation of Multi-Particulates C
    3.1. Mix Omeprazole and sodium bicarbonate in a high shear granulator for 5 minutes.
    3.2. Densify the powder mix from Step 3.1 using a roller compactor by forming compacted ribbons.
    3.3. Mill the ribbons from Step 3.2 using a FitzMill®
4. Blend the multi-particulates A from Step 1.2.5 with multi-particulates B from Step 2.3 and multi-particulates C from Step 3.3, crospovidone, portion of colloidal silica in a V-blender for 15 minutes.
5. Add magnesium stearate to the blend from Step 4 and mix for 5 minutes.
6. Compress the blend from Step 5 into tablets.

Example III

The following compositions may be prepared. The dosage form may include any combination or all of the above described five types of granules in a tablet, capsule or any other viable dosage form.

TABLE 7

Pharmaceutical Composition of Abuse deterrent formulation with over dose protection

| Granule type | Function | Tablet/Capsule (1-2) | Multiple Tablets/Capsules (~5) |
|---|---|---|---|
| Type A: Drug granules with pH dependent coating | Non crushable and non-extractable | Non crushable and non-extractable | |
| Type B: pH independent polymer | Gelling/Viscosity builder | Insignificant increase in viscosity | Significant increase in viscosity |
| Type C: Disintegrant granules | Tablet Disintegration and Increase in pH | Insignificant increase in pH | Significant increase in pH |
| Type D: pH dependent polymer | pH and Viscosity modifier | Insignificant increase in pH/viscosity | Significant increase in pH/viscosity |
| Type E: Ion exchange polymer | In-situ complex formation | No effect on release | Controlled release |

1. Type A Granules

TABLE 8

| | Composition of granules | | | |
|---|---|---|---|---|
| | Formula I | | Formula II | |
| Ingredients | (% w/w) | mg/dose | (% w/w) | mg/dose |
| Oxycodone Hydrochloride/Hydrocodone | 30.00 | 30.00 | 30.00 | 30.00 |
| Polyox ® N 80/Polyox ® WSR 1105/Polyox ® WSR N-303 | 63.18 | 63.18 | 53.06 | 53.06 |
| Hydroxypropyl methyl cellulose | — | — | 9.30 | 9.30 |
| Kollidon SR | — | — | 4.65 | 4.65 |
| Triethyl citrate | 6.32 | 6.32 | 2.79 | 2.79 |
| α-dl-Tocopherol | 0.50 | 0.50 | 0.20 | 0.20 |
| Total | 100.0 | 100.00 | 100.0 | 100.0 |

Manufacturing Procedure:
1. Spray the solution of α-dl-Tocopherol solution and triethyl citrate onto the POLYOX® N80/WSR 1105/WSR N-303 in a high shear granulator while mixing to achieve uniform powder mix using impeller and chopper at medium speeds.
2. Add Oxycodone Hydrochloride/Hydrocodone and other materials such as hydroxypropyl methyl cellulose, Kollidon SR to POLYOX blend from step #1, and subject to appropriate granulation process such as hot-melt extrusion, melt granulation, roller compaction, high shear or low shear mixing.
3. Subject granules from step #2 to appropriate delumping or size reduction process using co-mill, fitz mill, micro-pulvarizer or micronization.
4. Cure the granules if required.
5. Coat the granules with seal coat followed by functional coat.

TABLE 9

| | Composition of granules | |
|---|---|---|
| | Formula III | |
| Composition | (% w/w) | mg/dose |
| Microcrystalline cellulose Cellets | 85.00 | 300.00 |
| Oxycodone Hydrochloride/Hydrocodone | 8.50 | 30.00 |
| Methocel, Premium E5 | 5.66 | 20.00 |
| Talc | 0.85 | 3.00 |
| Purified water | 30.00 | NA |
| Ethyl Alcohol | 70.00 | NA |
| Total | | 353.00 |

Coating Procedure:
1. Add methocel E5 to ethyl alcohol taken in a suitable size stainless steel container and mix until dissolves.
2. Add half the quantity of water to solution in step #1 and mix for ~2 minutes.
3. Slowly add Oxycodone Hydrochloride/Hydrocodone to the above solution and mix until dissolves.
4. Homogenize talc with second half of water in a separate container for ~5 minutes.
5. Add talc dispersion (step #4) to the solution from step #3 and mix for at least 30 minutes or until it disperses.
6. Coat the cellets using a Wurster fluid bed coater with an inlet air temperature of 40°-50° C. and sufficient air volume for fluidization.

7. When the product temperature is reached to 30° C., start spraying the dispersion from Step #5 onto cellets while maintaining the product temperature of 28°-30° C. and sufficient air volume for the fluidization until the target coating weight gain is reached.
8. Dry the coated cellets from Step #7.

1.1. Seal Coating of Granules

TABLE 10

Formulation composition of seal coating of granules

| Composition | Formula I/II | | Formula III | |
|---|---|---|---|---|
| | (% w/w) | mg/dose | (% w/w) | mg/dose |
| Oxycodone Hydrochloride/ Hydrocodone (granules) | 83.33 | 100.00 | 94.13 | 353.00 |
| Methocel, Premium E5 | 11.90 | 14.28 | 4.19 | 15.70 |
| Triethyl citrate/Dibutyl sebacate | 1.19 | 1.43 | 0.21 | 0.80 |
| Talc/Magnesium trisilicate | 3.57 | 4.28 | 1.47 | 5.50 |
| Purified water | 30.00 | NA | 30.00 | NA |
| Ethyl Alcohol | 70.00 | NA | 70.00 | NA |
| Total | | 120.00 | | 375.00 |

Coating Procedure:
1. Add triethyl citrate or dibutyl sebacate to a mixture of alcohol and half of water taken in a suitable size stainless steel container and mix for ~2 min.
2. Slowly add Methocel and mix until dissolves.
3. Homogenize talc or magnesium trisilicate with second half of water in a separate container for ~5 minutes.
4. Add dispersion from step #3 to polymer solution (step #2) and mix for at least 30 minutes or until it disperses.
5. Coat the granules using a Wurster fluid bed coater with an inlet air temperature of 40°-50° C. and sufficient air volume for fluidization.
6. When the product temperature is reached to 30° C., start spraying the dispersion from Step #4 onto granules while maintaining the product temperature of 28°-30° C. and sufficient air volume for the fluidization until the target coating weight gain is reached.
7. Dry the coated granules from Step #6.

1.2. Functional Coating of Granules

TABLE 11

Formulation composition of functional coating

| Composition | Formula I/II | | Formula III | |
|---|---|---|---|---|
| | (% w/w) | mg/dose | (% w/w) | mg/dose |
| Seal coated granules | 71.43 | 120.00 | 83.4 | 375.00 |
| Eudragit EPO | 9.14 | 15.35 | 5.30 | 24.00 |
| Cellulose acetate | 13.71 | 23.03 | — | — |
| Ethocel Premium 10 | — | — | 8.00 | 36.00 |
| Talc/Magnesium trisilicate | 3.43 | 5.76 | 2.00 | 9.00 |
| Triethyl citrate/ Dibutyl sebacate | 2.29 | 3.85 | 1.30 | 6.00 |
| Solvent system for coating dispersion | | | | |
| Acetone | 90.00 | NA | — | — |
| Ethyl alcohol | — | — | 70.00 | NA |
| Purified water | 10.00 | NA | 30.00 | NA |
| Total | | 168.00 | | 450.00 |

Figure 7:
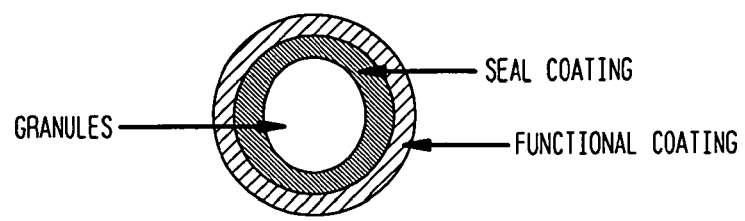
FIG. 7 is a schematic representation of an embodiment of multi-particulate A.

Coating Procedure:
1. Add Eudragrit EPO to acetone or ethyl alcohol taken in a suitable stainless steel container and mix until it dissolves.
2. To the solution in Step #1 add cellulose acetate or ethocel to and mix until it dissolves.
3. Add triethyl citrate or dibutyl sebacate to solution in step #2 while mixing.
4. Homogenize talc or magnesium trisilicate with water in a separate container for ~5 minutes.
5. Add dispersion from step #4 to solution (step #3) and mix for at least 30 minutes or until it disperses.
6. Coat the granules using a Wurster fluid bed coater with an inlet air temperature of 40°-50° C. and sufficient air volume for fluidization.
7. When the product temperature is reached to 30° C., start spraying the dispersion from Step #5 onto granules while maintaining the product temperature of 28°-30° C. and sufficient air volume for the fluidization until the target coating weight gain is reached.
8. Dry the coated granules from Step #7. A schematic illustration of multi-particulates A/Type A granules is shown in FIG. 7.

2. Type B Granules

TABLE 12

Formulation composition of Type B granules

| Composition | (% w/w) | mg/dose |
|---|---|---|
| Polyox ® WSR 1105/Polyox ® WSR N-303 | 90.45 | 135.68 |
| Triethyl citrate | 9.05 | 13.57 |
| α-dl-Tocopherol | 0.50 | 0.75 |
| Total | | 150.00 |

Manufacturing Procedure:
1. Spray the solution of α-dl-Tocopherol solution and triethyl citrate onto the POLYOX® WSR 1105/WSR N-303 in a high shear granulator while mixing to achieve uniform powder mix using impeller and chopper at medium speeds.
2. Subject the powder mix from step #1 to appropriate granulation process such as hot-melt extrusion, melt granulation, roller compaction, high shear or low shear mixing.
3. Subject granules from step #2 to appropriate delumping or size reduction process using co-mill, fitz mill, micro-pulvarizer or micronization.
4. Granules can be optionally coated with enteric polymers such as Eudragit® L 100-55, hypromellose phthalate (HPMCP), hypromellose acetate succinate (HPMCAS) etc.

3. Type C Granules

TABLE 13

Formulation composition of Type C granules

| Composition | (% w/w) | mg/dose |
|---|---|---|
| Microcrystalline cellulose | 6.00 | 13.50 |
| Croscarmellose sodium | 2.00 | 4.50 |

TABLE 13-continued

Formulation composition of Type C granules

| Composition | (% w/w) | mg/dose |
|---|---|---|
| Calcium Carbonate | 53.34 | 120.00 |
| Magnesium hydroxide | 33.33 | 75.00 |
| Alginic Acid | 5.33 | 12.00 |
| Total | | 225.00 |

Manufacturing Procedure:

1. In a high shear granulator take Microcrystalline cellulose, Croscaramellose sodium, Calcium Carbonate, Magnesium hydroxide and mix using impeller and chopper at medium speed to achieve uniform blend.
2. To the blend from step #1, spray water to achieve appropriate granules by high shear or low shear mixing.
3. Subject granules from step #2 to appropriate delumping or size reduction process using co-mill or fitz mill.
4. Dry the granules using a fluid bed dryer or air oven until the LOD is <1%.
5. In a high shear granulator, to the granules from step #4 add alginic acid and mix using impeller and chopper at medium speeds.

Dissolution Studies Using USP Apparatus II

Figure 8:
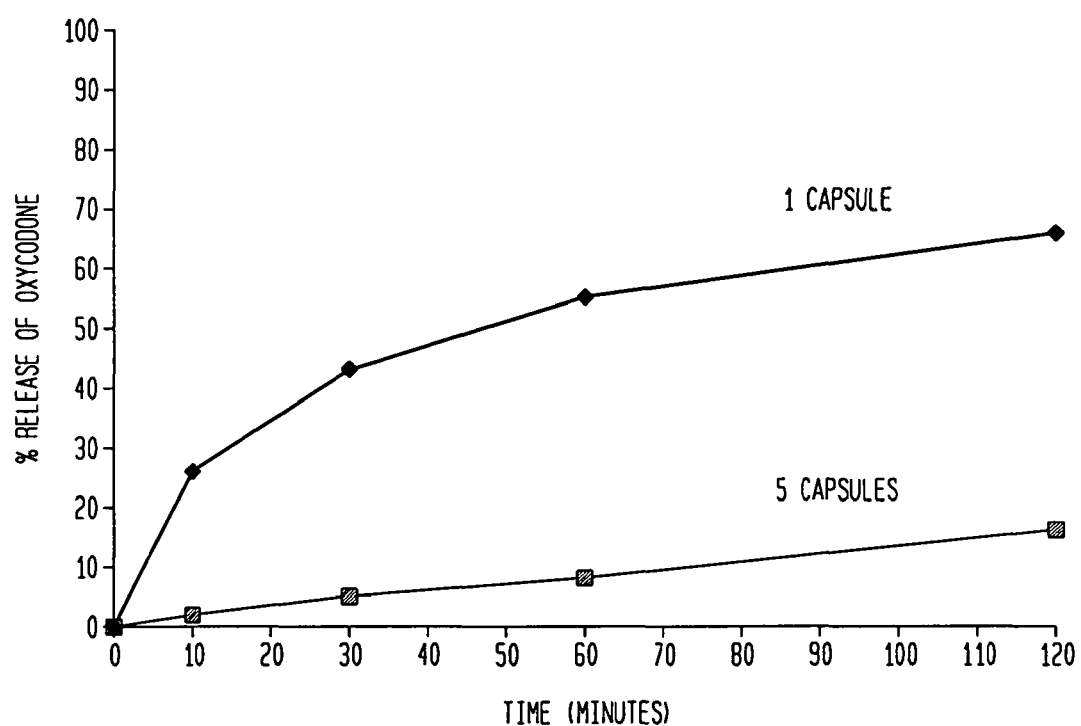
FIG. 8 is a graph that depicts the effect of single dose versus multiple doses on the percentage of oxycodone hydrochloride as the drug is released at time intervals of 10, 30, 60, and 120 minutes at a pH 1.6, wherein oxycodone hydrochloride is present at about 30% w/w of the multi-particulate A, and the composition contains equivalent amounts of multi-particulate A and extra-granular components in a capsule which is dissolved in a 250 ml of a medium with a pH of 1.6; as shown, the percentage of drug released is drastically reduced when multiple doses are administered.

The following experiment was done: take equivalent amounts of Type A granules and Type C granules in a capsule and perform dissolution studies in 250 mL of the medium (pH 1.6); and withdraw dissolution samples at 10, 30, 60 and 120 mins and analyze for % release of oxycodone. The results are illustrated in FIG. 8.

4. Type D Granules

TABLE 14

Formulation Composition of Type D granules

| Composition | (% w/w) | mg/dose |
|---|---|---|
| Carbopol 934P | 98.00 | 98.00 |
| Sodium hydroxide/Sodium bicarbonate | 2.00 | 2.00 |
| Alcohol | 95.00 | NA |
| Water | 5.00 | NA |
| Total | | 100.00 |

Manufacturing Procedure:

1. Add sodium hydroxide/sodium bicarbonate to water taken in a stainless steel vessel and mix until dissolved. To this solution add alcohol and mix for few minutes.
2. Spray this solution on to Carbopol in a high shear granulator while mixing using impeller and chopper at medium speeds.
3. Subject the blend from step #2 to appropriate granulation process such roller compaction, high shear or low shear mixing.
4. Subject granules from step #3 to appropriate delumping or size reduction process using co-mill or fitz mill.
5. Dry the granules from step #4 using a fluid bed dryer or air oven.
6. Granules can be optionally coated with enteric polymers such as Eudragit® L 100-55, hypromellose phthalate (HPMCP), hypromellose acetate succinate (HPMCAS) etc.

5. Type E Granules

Binding Studies Using USP Apparatus I

The following experiment was done.

Figure 9:
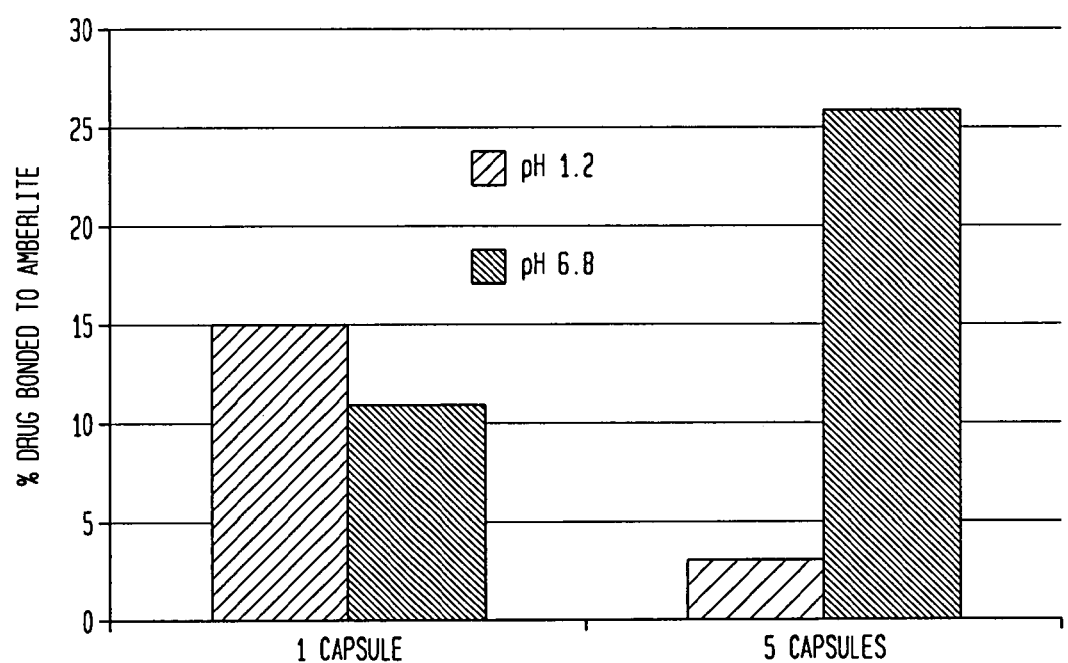
FIG. 9 is a bar graph that depicts the effects of single dose versus multiple doses on the percentage of naloxone hydrochloride bonded to an ion exchange polymer which in this case is Amberlite, at different pH conditions; as shown, the percentage of naloxone hydrochloride bonded to the Amberlite drastically increases when multiple doses of the drug is administered, thus providing overdose protection.

1. Based on the 1:1 molar ratio of naloxone:Amberlite™ IRP64, take the required quantity of naloxone and Amberlite™ IRP64 blend in a capsule and add it to 500 mL of the medium (0.1 N HCl/5 mM Phosphate buffer, pH 6.8).
2. Withdraw dissolution samples at 10, 30 and 60 mins.
3. Centrifuge the samples at 3000 rpm for 10 mins and filter through fritted filter (40-60° C.) to get the supernatant for analysis. The results are illustrated in FIG. 9.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A solid oral multi-particulate dosage form providing overdose protection comprising:
    a) a crush-resistant first population of particulates, having a first population total weight, and comprising an opioid embedded in a polymer matrix, and at least one coating layer over the polymer matrix;
    wherein the polymer matrix comprises a polyethylene oxide polymer, and
    wherein the at least one coating layer comprises a pH-dependent cationic polymer and a nonionic polymer; and
    b) a second population of particulates comprising a viscosity-building polymer; wherein the viscosity-building polymer is present in an amount of about 30 to about 80 weight %, based on the total weight of the dosage form; and
    c) a third population of particulates comprising an alkaline buffering agent;
    wherein the alkaline buffering agent is present in an amount of about 20 to about 40 weight %, based on the total weight of the dosage form,
    wherein when one unit dose of the dosage form is swallowed whole by an individual, as prescribed, the alkaline buffering agent will release in gastric fluid without impact to opioid release;
    wherein when multiple unit doses of the dosage form are swallowed whole by the individual in amounts that are non-prescribed, the alkaline buffering agent will release in gastric fluid and increase gastric fluid pH to greater than about 5, at which pH the cationic polymer in the at least one coating layer becomes insoluble, providing overdose protection by retarding dissolution of the opioid from the polymer matrix through the pH-dependent cationic polymer in the coating, and
    wherein the pH-dependent cationic polymer in the coating retards opioid release in intestinal fluids.

2. The dosage form of claim 1, wherein the polyethylene oxide polymer has a molecular weight of about 100,000 to about 7,000,000 g/mol.

3. The dosage form of claim 1, wherein the polymer matrix further comprises at least one additional nonionic polymer selected from the group consisting of hydroxypropylcellulose, hydroxypropyl methylcellulose, hydroxyethylcellulose, ethylcellulose, cellulose acetate butyrate, and cellulose acetate.

4. The dosage form of claim 1, wherein the cationic polymer is a copolymers based on dimethylaminoethyl methacrylate, butyl methacrylate, and methyl methacrylate.

5. The dosage form of claim 2, wherein the polyethylene oxide polymer has a molecular weight of about 4,000,000 g/mol.

6. The dosage form of claim 1, wherein the viscosity-building polymer is selected from the group consisting of polyethylene oxide polymers, pectin, polysaccharides, crosslinked starches, silicone polymers, carbomers, sodium carboxymethylcellulose, polycarbophil tragacanth, xanthan gum, and combinations thereof.

7. The dosage form of claim 6, wherein the viscosity-building polymer is a nonionic polymer selected from the group consisting of polyethylene oxide polymers having a molecular weight of about 100,000 to about 7,000,000 g/mol, polysaccharides, silicone polymers, and polycarbophil tragacanth.

8. The dosage form of claim 1, wherein the alkaline buffering agent is sodium bicarbonate or magnesium hydroxide.

9. The dosage form of claim 1, wherein the first population of particulates further comprises a plasticizer and a surfactant.

10. The dosage form of claim 9, wherein the plasticizer is contained in the polymer matrix, the coating layer, or both the polymer matrix and the coating layer.

11. The dosage form of claim 9, wherein the plasticizer is selected from the group consisting of triethyl citrate, propylene glycol, dibutyl sebacate, and polyethylene glycol.

12. The dosage form of claim 9, wherein the surfactant comprises dioctyl sodium sulfosuccinate, PEG-40 hydrogenated castor oil, or a combination thereof.

13. The dosage form of claim 1, wherein the first population of particulates further comprises an intermediate coating layer disposed between the polymer matrix and the at least one coating layer.

14. The dosage form of claim 13, wherein the intermediate coating layer comprises a mixture of methylcellulose and hydroxypropyl methylcellulose.

15. The dosage form of claim 1, wherein the opioid is selected from the group consisting of codeine, phenazocine, tilidine, tramadol, meperidine, sufentanil, prodine, methadone, pentazocine, oxycodone, oxymorphone, hydrocodone, hydromorphone, tapentadol, morphine, buprenorphine, and fentanyl.

16. The dosage form of claim 1, further comprising a disintegrant, wherein the disintegrant is present in the third population of particulates, and/or is present as an extra-granular component in the dosage form.

17. The dosage form of claim 16, wherein the disintegrant is selected from the group consisting of carmellose calcium, carboxymethylstarch sodium, croscarmellose sodium, crospovidone, sodium starch glycolate, colloidal silicon dioxide, alginic acid, and a combination of two or more thereof.

18. The dosage form of claim 1, further comprising a fourth population of particulates comprising a pH-dependent viscosity-building polymer and a fourth population alkaline buffering agent.

19. The dosage form of claim 18, further comprising a fifth population of particulates comprising an ion exchange polymer.

20. The dosage form of claim 19, further comprising a sixth population of particulates comprising an acid suppressing agent.

21. The dosage form of claim 1, further comprising an opioid antagonist selected from the group consisting of naloxone, naltrexone, nalmefene, nalidixic acid, nalmexone, and nalorphine.

22. The dosage form of claim 1, wherein the dosage form is a tablet, an orally disintegrating tablet, or a capsule.

23. The dosage form of claim 1, wherein the viscosity-building polymer increases gastric fluid viscosity when multiple units of the dosage form are swallowed whole by the patient.

24. The dosage form of claim 1, wherein the individual is a patient and/or an abuser.

* * * * *